United States Patent [19]
Ishizaki et al.

[11] Patent Number: 5,629,265
[45] Date of Patent: May 13, 1997

[54] CYANOKETONE DERIVATIVE AND HERBICIDE CONTAINING IT AS AN ACTIVE COMPONENT

[75] Inventors: Masahiko Ishizaki, Tsukuba; Seiji Nagata, Tokuyama; Junji Takenaka, Tsukuba, all of Japan

[73] Assignee: Tokuyama Corporation, Tokuyama, Japan

[21] Appl. No.: 264,151

[22] Filed: Jun. 22, 1994

[51] Int. Cl.$^6$ .................. C07C 255/17; C07C 255/27; A01N 37/34; A01N 43/08; A01N 43/10; A01N 43/12; A01N 43/16; A01N 43/18; A01N 43/38; A01N 43/40; A01N 43/50; A01N 43/52; A01N 43/54; A01N 43/60; A01N 43/647; A01N 43/707

[52] U.S. Cl. .................. 504/249; 504/224; 504/225; 504/227; 504/229; 504/230; 504/235; 504/239; 504/240; 504/244; 504/246; 504/247; 504/248; 504/251; 504/252; 504/257; 504/261; 504/266; 504/267; 504/269; 504/270; 504/271; 504/276; 504/275; 504/277; 504/279; 504/280; 504/282; 504/283; 504/284; 504/288; 504/289; 504/292; 504/294; 504/298; 504/312; 544/133; 544/152; 544/182; 544/215; 544/283; 544/284; 544/298; 544/333; 544/353; 544/354; 544/367; 546/114; 546/115; 546/116; 546/153; 546/193; 546/194; 546/201; 546/207; 546/208; 546/210; 546/211; 546/226; 546/242; 546/290; 548/170; 548/182; 548/187; 548/213; 548/217; 548/221; 548/225; 548/228; 548/229; 548/243; 548/255; 548/306.4; 548/307.1; 548/312.4; 548/314.7; 548/316.4; 548/324.1; 548/365.7; 548/370.1; 548/484; 548/517; 548/527; 548/541; 548/542; 548/543; 548/551; 549/28; 549/52; 549/62; 549/416; 549/420; 549/437; 549/449; 558/389; 558/392; 558/396

[58] Field of Search .................. 558/389, 392, 558/396; 546/290, 226, 194, 116, 114, 153; 504/249, 312, 235, 251, 257, 246, 294, 282, 270, 299, 289, 266, 271, 283, 277, 269, 247, 292, 288, 239, 227, 267, 230, 298, 284, 276; 544/367, 298, 333, 182, 215, 354, 283, 284; 548/541, 527, 314.7, 170, 316.4, 307.1, 312.4, 306.4, 365.7, 484, 366.1, 213, 225, 243, 182, 187, 221, 217, 255; 549/449, 62, 416, 28, 437, 52

[56] References Cited

U.S. PATENT DOCUMENTS 4,531,969 7/1985 Nestler et al. .................. 560/21
5,234,894 8/1993 Ishizaki et al. .................. 504/224

FOREIGN PATENT DOCUMENTS 0270378 6/1988 European Pat. Off. .
0506373 9/1992 European Pat. Off. .
0109483 5/1994 European Pat. Off. .
2223894 12/1973 Germany .
2046753 11/1980 United Kingdom .

OTHER PUBLICATIONS

Abstract of Japanese Laid–Open Application 54525/May 1974.
Abstract of Japanese Laid–Open Application 2237/Feb. 1979.
Abstract of Japanese Laid–Open Application 11452/Jan. 1985.
Chemical Abstract, 102, No. 25, 220 443 (Abstract of Japanese Kokai 60–008,253). (Month Not Available) 1985.
Thornber, Chemical Society Reviews, vol. 8, No. 1, @1979, pp. 563–580.

*Primary Examiner*—Johann Richter
*Assistant Examiner*—Laura L. Stockton
*Attorney, Agent, or Firm*—Sherman and Shalloway

[57] ABSTRACT

Disclosed herein are cyanoketone derivatives of the following formula (1)

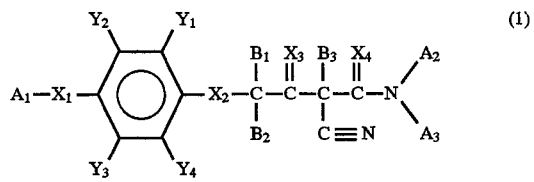

such as 1-cyano-1-piperidinocarbonyl-3-[4-(2-chloro-4-trifluoromethylphenoxy)phenoxy]-2-butanone, 1-cyano-1-piperidinocarbonyl-3-[4-(3-chloro-5-trifluoromethyl-2-pyridyloxy)phenoxy]-2-butanone, 1-cyano-1-(N-methyl-N-dichlorophenyl)aminocarbonyl-3-[4-(2-quinoxalyloxy) phenoxy]-2-butanone, 1-cyano-1-(N,N-dibutyl) aminocarbonyl-3-[4-(3-chloro-5-trifluoromethyl-2-pyridyloxy)phenoxy-2-butanone, and the like, which are characterized by excellent herbicidal activity and effectiveness against a variety of gramineous weeds.

23 Claims, No Drawings

CYANOKETONE DERIVATIVE AND HERBICIDE CONTAINING IT AS AN ACTIVE COMPONENT

DETAILED DESCRIPTION OF THE INVENTION

The present invention relates to a cyanoketone derivative and a herbicide containing it as an active component.

A variety of compounds have been tested on their herbicidal activities, and many herbicidal compounds are commercially available.

Japanese Laid-open Patent Application No. 54525/1974 discloses that a herbicide prepared by combining a compound of the following formula (2)

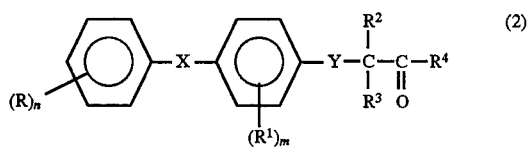

wherein R is H, halogen, $C_1$-$C_4$ alkyl, $C_1$-$C_4$ alkoxy or alkylthio, cyclohexyl, cyclopentyl or phenyl, $R^1$ is H, halogen, $C_1$-$C_4$ alkyl or $C_2$-$C_4$ alkenyl, each of X and Y is oxygen or sulfur, each of n and m is an integer of 1 to 30, $R^2$ is H, $C_1$-$C_{10}$ alkyl, $C_2$-$C_6$ alkoxyalkyl, $C_2$-$C_4$ alkylamine or phenyl, $R^3$ is H or $C_1$-$C_4$ alkyl, $R^4$ is —OH, —O—$C_1$-$C_{10}$ alkyl, —S—$C_1$-$C_6$ alkyl, O—$C_2$-$C_4$ alkenyl, —O-cyclohexyl, —O-cyclopentyl, phenoxy or phenylthio which may be substituted with one or two halogen atoms, —$NH_2$, —NH—$C_1$-$C_4$ alkyl, —N-di($C_1$-$C_4$)alkyl,

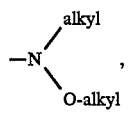

halogen, —$CF_3$, —NH-phenyl substituted with —$OCF_2CF_2H$ or —$COOCH_3$, —O-benzyl, —NH-benzyl, —S-benzyl or —O-kat (kat is an inorganic or organic cation), for example, the compound of the following formula (3)

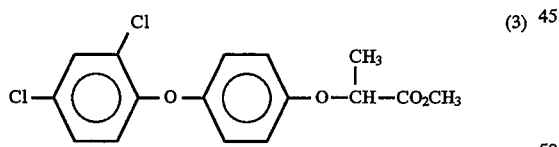

(commercially available under the trade name of "Hoelon") with an auxiliary exhibits an effect on grasses (gramineous plants).

Ex-West Germany Laid-open Patent Application No. 2,812,571 and its corresponding Japanese Laid-open Patent Application No. 22371/1979 disclose that the trifluoromethylpyridoxyphenoxypropionic acid derivative of the following formula (4)

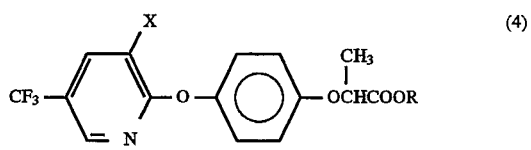

wherein X is H or Cl, R is H, lower alkyl, lower alkenyl, cycloalkyl, a salt-forming atom or a salt-forming moiety, for example, the compound of the following formula (5)

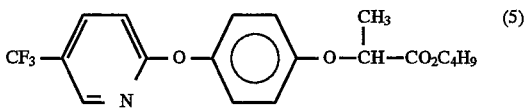

(commercially available under the trade name of "Fusilade"), exhibits a herbicidal effect on gramineous weeds.

On the other hand, Japanese Laid-open Patent Application No. 11452/1985 discloses a-cyanoketones of the following formula (6)

which are a compound of the above formula (6) in which $R_1$ is an alkyl group or an aromatic group and $R_2$ is an alkyl group having at least 3 carbon atoms, an aralkyl group, an aromatic group or a heterocyclic group and a compound of the formula (6) in which $R_1$ is a heterocyclic group, a substituted phenoxy or substituted thiophenoxy group and $R_2$ is a hydrogen atom, an alkyl group, an aromatic group or a heterocyclic group, and that such α-cyanoketones exhibit an effect on a variety of weeds such as southern crabgrass, barnyardgrass, tufted knotweed and slender amaranth when these are applied in a high dosage (foliar application test).

Some of the present inventors have found a cyanoketone derivative and herbicide containing it as an active component represented by the following formula (7) and have already proposed this finding (see U.S. Pat. No. 5,234,894).

The cyanoketone derivative of the following formula (7) has remarkably high herbicidal activity and is effective against a variety of gramineous weeds. Examples of the weeds against which the herbicidal activity is generally effective include upland soil gramineous weeds such as fall panicum, green foxtail, sorghum, wild oat, Japanese brome, water foxtail, annual bluegrass, barnyardgrass, Johnsongrass, quackgrass, southern crabgrass, goosegrass, Italian ryegrass, burmudagrass and knotgrass.

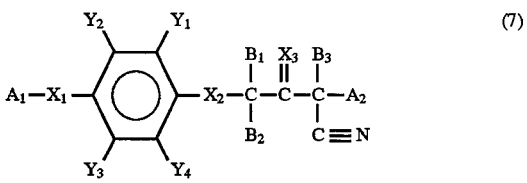

wherein $A_1$ is a substituted or unsubstituted phenyl or naphthyl group, or a substituted or unsubstituted heterocyclic group selected from the group consisting of a 5-membered ring, a 6-membered ring, a 5- and 6-membered fused ring group and a 6- and 6-membered fused ring group, substituents of said substituted phenyl, naphthyl and heterocyclic groups being selected from the group consisting of a halogen atom, an alkyl group having 1 to 4 carbon atoms, a halogenoalkyl group having 1 to 4 carbon atoms, an alkoxy group having 1 to 4 carbon atoms, an alkylthio group having 1 to 4 carbon atoms, and alkoxycarbonyl group having 1 to 6 carbon atoms, a nitro group and a cyano group; each of $X_1$, $X_2$ and $X_3$ is independently an oxygen or sulfur atom; each of $B_1$, $B_2$ and $B_3$ is independently a hydrogen atom or alkyl group having 1 to 6 carbon atoms; each of $Y_1$, $Y_2$, $Y_3$ and $Y_4$ is independently a hydrogen atom, a halogen atom or alkyl group having 1 to 6 carbon atoms; and $A_2$ is substituted or unsubstituted group selected from the group consisting of an alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms and an alkoxycarbonyl group having 1 to 6 carbon atoms, substituents of said substituted groups being selected from the group consisting of a halogen atom, an alkoxy group having 1 to 4 carbon atoms, an alkylthio group having 1 to 4 carbon atoms, a tetrahydrofuryl group and a cyano group; and unsubstituted benzoyl group; a halogen substituted benzoyl group; a cyano group of the group as defined in $A_1$; provided that when $B_1$ is a hydrogen atom and $B_2$ is alkyl, the compound of the formula (7) is an R- or S-enantiomers with regard to the asymmetric carbon to which $B_1$ and $B_2$ are bonded or a mixture of these enantiomers.

It is an object of the present invention to provide a novel cyanoketone derivative.

It is another object of the present invention to provide a herbicide containing the cyanoketone derivative of the present invention as a herbicidal active component.

It is further another object of the present invention to provide a novel cyanoketone derivative which exhibits high selectivity and high herbicidal activity and a herbicide containing this derivative.

It is still further another object of the present invention to provide a herbicide which has high herbicidal activity on grasses even when used in a low dosage and which is much safe even when applied to intended crop in a high dosage.

Other objects and advantages of the present invention will be apparent from the following description.

According to the present invention, the above objects and advantages of the present invention are achieved, first, by a cyanoketone derivative of the following formula (1)

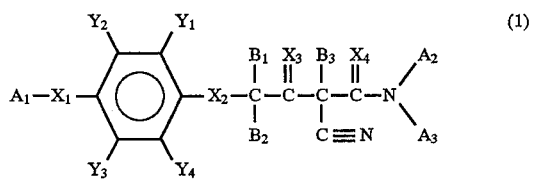

wherein $A_1$ is a substituted or unsubstituted phenyl or naphthyl group, or a substituted or unsubstituted heterocyclic group selected from the group consisting of a 5-membered ring, a 6-membered ring, a 5- and 6-membered fused ring group and a 6- and 6-membered fused ring group, substituents of said substituted phenyl, naphthyl and heterocyclic groups being selected from the group consisting of a halogen atom, an alkyl group having 1 to 4 carbon atoms, a halogenoalkyl group having 1 to 4 carbon atoms, an alkoxy group having 1 to 4 carbon atoms, an alkylthio group having 1 to 4 carbon atoms, an alkoxycarbonyl group having 1 to 6 carbon atoms, a nitro group and a cyano group; each of $X_1$, $X_2$, $X_3$ and $X_4$ is independently an oxygen or sulfur atom; each of $B_1$, $B_2$ and $B_3$ is independently a hydrogen atom or alkyl group having 1 to 6 carbon atoms; each of $Y_1$, $Y_2$, $Y_3$ and $Y_4$ is independently a hydrogen atom, a halogen atom or alkyl group having 1 to 6 carbon atoms; and each of $A_2$ and $A_3$ is independently selected from the group consisting of a hydrogen atom, a substituted or unsubstituted alkyl group having 1 to 6 carbon atoms, an alkenyl group having 2 to 6 carbon atoms, an alkoxy group having 1 to 4 carbon atoms, an alkylthio group having 1 to 4 carbon atoms, an alkoxycarbonyl group having 2 to 6 carbon atoms, a cyano group and a group as defined in $A_1$; substituents of said substituted alkyl group being selected from the group consisting of a halogen atom, an alkoxy group having 1 to 4 carbon atoms, an alkylthio group having 1 to 4 carbon atoms, a cyano group, a phenyl group and a heterocyclic group of a 5- or 6-membered ring; provided that both $A_2$ and $A_3$ can form a saturated or unsaturated ring which may contain a hereto atom and that when $B_1$ is a hydrogen atom and $B_2$ is alkyl, the compound of the formula (1) is an R- or S-enantiomer with regard to the asymmetric carbon to which $B_1$ and $B_2$ are bonded or a mixture of these enantiomers.

The cyanoketone derivative represented by the formula (1) of the present invention has a strong herbicidal activity compared to the cyanoketone derivative of the formula (7) which is described in said U.S. Pat. No. 5,234,894, and therefore exhibits a herbicidal activity to a variety of gramineous weeds in a smaller amount.

In the above formula (1), $A_1$ is a substituted or unsubstituted aromatic group, or a substituted or unsubstituted heterocyclic group.

The aromatic group preferably includes phenyl and naphthyl.

The heterocyclic group preferably includes five-membered or six-membered cyclic groups having at least one hetero atom selected from the group consisting of oxygen, sulfur and nitrogen atoms.

Examples of such heterocyclic groups preferably include five-membered cyclic groups such as furyl, thienyl, pyrrolyl, imidazolyl, pyrazolyl, oxazolyl, thiazolyl, isooxazolyl and isothiazolyl groups; six-membered ring groups such as pyridyl, pyranyl, thiopyranyl, pyrazinyl, pyrimidinyl, triazinyl and cyclohexenyl groups; five- or six-membered fused ring groups such as benzofuranyl, benzothienyl, indolyl, benzimidazolyl, benzothiazolyl, benzoxazolyl, oxazolopyridinyl and thiazolopyridinyl groups; and six- or six-membered fused ring groups such as quinolyl, quinoxalinyl and quinazolinyl groups.

The substituent which may be substituted on these aromatic and heterocyclic groups includes a halogen atom such as chlorine, bromine, iodine and fluorine; an alkyl group having 1 to 4 carbon atoms such as methyl, ethyl, propyl and butyl; a halogenoalkyl group having 1 to 4 carbon atoms such as chloromethyl, difluoromethyl, trifluoromethyl, trifluoroethyl, perfluoroethyl, pentachloropropyl and perfluorobutyl; an alkoxy group having 1 to 4 carbon atoms such as methoxy, ethoxy, propoxy and butoxy; an alkylthio group having 1 to 4 carbon atoms such as methylthio, ethylthio, propylthio and butylthio; an alkoxycarbonyl group having 1 to 6 carbon atoms such as methoxycarbonyl, ethoxycarbonyl, propoxycarbonyl and butoxycarbonyl; a nitro group; and a cyano group. These substituents are preferred particularly from an industrial point of view.

With respect to $A_1$, the heterocyclic group gives a higher herbicidal activity than the aromatic group. Above all, a compound in which the hetterocyclic ring is a pyridyl group shows an especially high herbicidal activity. The most preferable pyridyl group has a trifluoromethyl group at the S-position and a halogen atom at the 3-position.

In the formula (1), each of $X_1$, $X_2$, $X_3$ and $X_4$ is, independently of the other, an oxygen or sulfur atom. In particular, an oxygen atom is preferred.

In the formula (1), each of $Y_1$, $Y_2$, $Y_3$ and $Y_4$ is, independently of the others, a hydrogen atom, a halogen atom or alkyl and in particular a hydrogen atom is preferred.

The halogen atom includes chlorine, bromine, iodine and fluorine. The alkyl may be linear or branched, and is preferably selected from an alkyl group having 1 to 6 carbon atoms such as methyl, ethyl, propyl, butyl, heptyl and hexyl.

In the formula (1), each of $B_1$, $B_2$ and $B_3$ is, independently of the others, a hydrogen atom or alkyl. The alkyl preferably include a linear or branched alkyl group having 1 to 6 carbon atoms. Examples of the alkyl group include those specified concerning $Y_1$. With respect to $B_1$, the alkyl group is preferable and the methyl group is especially preferable, to the hydrogen atom. It is preferred that both $B_2$ and $B_3$ are a hydrogen atom.

In the formula (1), each of $A_2$ and $A_3$ is independently an atom or a group selected from the group consisting of a hydrogen atom, a substituted or unsubstituted alkyl, alkenyl, alkoxy, alkylthio, alkoxycarbonyl, substituted or unsubstituted benzoyl, cyano, a substituted or unsubstituted aromatic group or a substituted or unsubstituted heterocyclic group. Both $A_2$ and $A_3$ can form a saturated or unsaturated ring which may contain a hereto atom.

The alkyl preferably includes a linear or branched alkyl group having 1 to 6 carbon atoms. The alkenyl preferably includes a linear or branched alkenyl group having 2 to 6 carbon atoms. The alkoxy preferably includes a linear or branched alkoxy group having 1 to 4 carbon atoms. The alkylthio preferably includes a linear or branched alkylthio group having 1 to 4 carbon atoms. The alkoxycarbonyl preferably includes an alkoxy carbonyl group having 2 to 6 carbon atoms. The aromatic and heterocyclic groups and substitutents thereon are preferably selected from those specified concerning $A_1$.

The alkyl group includes those specified concerning $Y_1$.

The substituent which may be substituted on the alkyl preferably includes a halogen atom, an alkoxy group having 1 to 4 carbon atoms, an alkylthio group having 1 to 4 carbon atoms, a cyano group, a phenyl group or a heterocyclic group of 5- or 6-membered ring.

The alkenyl group preferably includes ethenyl, propenyl, butenyl, pentenyl and hexenyl.

The alkoxy group preferably includes methoxy, ethoxy, propoxy and butoxy.

The alkylthio group preferably includes methylthio, ethylthio, propylthio and butylthio.

The alkoxycarbonyl group preferably includes methoxycarbonyl, ethoxycarbonyl, propoxycarbonyl and butoxycarbonyl.

When $A_2$ and $A_3$ together form a saturated or unsaturated ring which may contain a hetero atom, a nitrogen atom or an oxygen atom is used as the hereto atom and further an alkyl chain or an alkynyl chain required for forming a ring having 2 to 8 carbon atoms is preferably used. Specific examples of a cyclic group formed by $A_2$ and $A_3$ with the nitrogen atom bonded to $A_2$ and $A_3$ include ethyleneimino, pyrrolidyl, pyrrolyl, pyrrolinyl, pyrazyl, pyrazolinyl, imidazolyl, triazolyl, piperldino, morpholino, piperazinyl, indolyl and plynyl groups.

Among the above-described definitions of $A_2$ and $A_3$, the compound in which $A_2$ and $A_3$ together form the above ring is preferred because of its high herbicidal activity.

Further, in the present invention, when $B_1$ is a hydrogen atom and $B_2$ is alkyl, the compound of the formula (1) is an R- or S-enantiomer with regard to the asymmetric carbon to which $B_1$ and $B_2$ are bonded or a mixture of these enantiomers.

The compound of the above formula (1) preferably include the following compounds.

(100) 1-cyano-1-(1-piperidylcarbonyl)-3-[4-(2-chloro-4-trifluorophenoxy)phenoxy]-2-butanone, (102) 1-cyano-1-(1-pyrrolidylcarbonyl)-3-[4-(4-bromophenoxy)phenoxy]-2-butanone, (104) 1-cyano-1-[1-(4-methyl)piperazinylcarbonyl]-3-(3,5-dibromo-4-phenoxyphenoxy)-2-pentanone, (106) 1-cyano-1-(1-pyrrolylcarbonyl)-3-(4-naphthoxyphenoxy)-3-butanone, (108) 1-cyano-1-(1-morpholinocarbonyl)-3-(4-naphthoxy)acetone, (110) 1-cyano-1-(N-butoxycarbonyl-N-methyl)aminocarbonyl-3-[4-(5-methyl-2-thienyloxy)phenoxy]-2-butanone, (112) 1-cyano-1-(N,N-dipropyl)aminocarbonyl-3-[4-(2-furiloxy)phenoxy]-2-butanone, (114) 1-cyano-1-[N,N-(3-dichlorophenyl)]aminocarbonyl-3-methyl-3-[4-(4-nitrophenoxy)phenoxy]-2-butanone, (116) 1-cyano-1-[1-(4-methyl)piperazinylcarbonyl]-3-[4-(4-methylthio-2-naphthyloxy)acetone, (118) 1-cyano-1-(pyrrolidylcarbonyl)-3-[4-(3-methoxy-2-thienyloxy)phenoxy]-2-butanone, (120) 1-cyano-1-(1-morpholinocarbonyl)-3-[2,6-dichloro-4-(5-fluoro-2-furiloxy)phenoxy]acetone.

(122) 1-cyano-1-[1-(3-methyl)pyrrolylcarbonyl]-3-[4-(N-methyl-3-methoxycarbonyl-2-pyrrolyloxy)-phenoxy]-2-butanone, (124) 1-cyano-1-(N-ethylthiomethyl-N-methyl)aminocarbonyl-3-[4-(2-imidazolyloxy)phenoxy]-2butanone, (126) 1-cyano-1-(N-2-tetrahydrofuryl)aminocarbonyl-3-[4-(3-pyrazolyloxy)phenoxy]-2-butanone.

(128) 1-cyano-1-(1-pyrazolylcarbonyl)-3-[4-(4-ethoxycarbonyl-2-oxazolyloxy)phenoxy]-2-butanone, (130) 1-cyano-1-[N-(5-chlorobenzofuryl)-N-methyl]aminocarbonyl-3-[4-(4-butoxycarbonyl-2-thiazolyloxy)phenoxy]-2-butanone, (132) 1-cyano-1-[1-(3,5-dimethyl)piperidinocarbonyl]-3-[4-(3-isothiazolyloxy)phenoxy]-2-butanone, (134) 1-cyano-1-(1-pyrrolidyl)carbonyl-3-[4-(3-isoxazolyloxy)phenoxy]-2-butanone, (136) 1-cyano-1-(N,N-dibutoxy)aminocarbonyl-3-[4-(1-methyl-3-iodo-2-pyrrolyloxy)phenoxy]butan-2 -thione, (138) 1-cyano-1-[1-(2,6-dimethyl)piperidinocarbonyl]-3-[4-(1-methyl-4-ethyl-2-pyrazolyloxy)phenoxy-2-pentanone.

(140) 1-cyano-1-[N-(4-nitrophenyl)-N-methyl]aminocarbonyl-3-[2-methyl-4-(1-methyl-3-pyrazolyloxy)phenoxy]-2-butanone, (142) 1-cyano-1-(1-pyrazonyl)carbonyl-3-[4-(2-oxazoyloxyoxy)phenoxy]-2-butanone, (144) 1-cyano-1-[N-(4-cyanophenyl)-N-methoxycarbonyl]aminocarbonyl-3-[4-(4-ethylthio-2-thiazolyloxy)-phenylthio]butan-2-thione, (146) 1-cyano-1-(1-morpholinocarbonyl)-3-[4-(3-isothiazolyloxy)phenoxy]-1-methyl-2-butanone, (148) 1-cyano-1-(N-phenyl-N-chloromethyl)aminocarbonyl-3-[4-(3-isoxazolyloxy)phenoxy]acetone, (150) 1-cyano-1-(1-piperidinocarbonyl)-3-[4-(3-chloro-5-trifluoromethyl-2-pyridyloxy)phenoxy]-2-butanone, (150a) R-enantiomer of 1-cyano-1-(1-piperidinocarbonyl)-3-[4-(5-trifluoromethyl-2-pyridyloxy)phenoxy]-2-butanone.

(150b) S-enantiomer of 1-cyano-1-(1-piperidinocarbonyl)- 3-[4-(5-trifluoromethyl-2-pyridyloxy)phenoxy]-2-butanone, (152) 1-cyano-1-[-5-chlorobenzoxazolyl)-N-methylamonocarbonyl-3-[4-(3,5-dichloro-2-pyridyloxy)phenoxy]-2-butanone, (154) 1-cyano-1-(2-pyrolidyl)carbonyl-3-[4-(3-chloro-5-trifluoromethyl-2-pyridyloxy)phenoxy]-2-butanone, (156) 1-cyano-1-(N-benzothiazolyl)aminocarbonyl-4-[4-(5-trifluoromethyl-2-pyridyloxy)phenoxy]-3-butanone, (158) 1-cyano-1-(1-pyrazolydinyl)carbonyl-3-[4-(2-pyridyloxy)phenoxy]acetone, (160) 1-cyano-1-(1-piperidinocarbonyl)-3-[4 -(6-propyl-2-pyranyloxy)phenoxy]acetone, (162) 1-cyano-1-(1-pyrrolidyl)carbonyl-3-[4-(5-cyano-2-pyridyloxy)phenoxy]-2-pentanone, (164) 1-cyano-1-[N-ethyl-N-(4,6-dimethylpyrimldyl) aminocarbonyl-3-[4-(2-pyraziloxy)phenoxy]-2-butanone, (166) 1-cyano-1-(1-imidazolyl)carbonyl-3-[2,6-dichloro-4-(2-pyranyloxy)phenoxy]-2-butanone, (168) 1-cyano-1-(1-piperidinocarbonyl)-3-[4-(6-methoxy-2-thiopyranyloxy)phenoxy]-2-butanone, (170) 1-cyano-1-(1-piperidinocarbonyl)-3-[4-(4,6-dimethoxy-2-pyridyloxy)phenoxy]-2-butanone, (172) 1-cyano-1-[(N-butyl-N-ethoxycarbonyl) aminocarbonyl]-3-[4-(4,6-dibutyl-2-triazinyloxy)phenoxy]-2-butanone, (174) 1-cyano-1-[1-(1,2,3-triazolyl)]-carbonyl-3-[4-(2-cyclohexyloxy)-2,3,5,6-tetrafluorophenoxy]-2-butanone, (176) 1-cyano-1-[1-(1,2,3-triazolyl)]-carbonyl-3-[4-(4-bromo-2-benzofuriloxy)phenoxy]-2-butanone, (178) 1-cyano-1-(N-furil-N-methyl)aminocarbonyl-3-[4-(3-chloromethyl-2-benzothienyloxy)phenoxy]-3-butanone, (180) 1-cyano-1-[1-(3,5-dimethyl)piperidinocarbonyl]-3-[4-(1,3-dimethyl-2-indolyloxy)phenoxy]-3-butanone, (182) 1-cyano-1-[N-propyl-N-(S-methylthio-2-pyridyl)] aminocarbonyl-3-[4-(6-ethyl-2-thiopyranyloxy)phenoxy]-3-butanone, (184) 1-cyano-1-[1-(4-methyl)piperazinylcarbonyl]-3-[4-(4,6-dimethyl-2-pyrimidyloxy)phenoxy]-2-butanone, (186) 1-cyano-1-[N-phenyl-N(methoxycarbonyl)phenyl] aminocarbonyl-3-[4-(2-triazinyloxy)phenoxy]-2-butanone.

(188) 1-cyano-1-(1-pyrrolyl)carbonyl-3-[4-cyclohexyloxy-3,5-dichlorophenoxy]acetone, (190) 1-cyano-1-[1-(4-methyl)piperazinylcarbonyl]-3-[4-(5-methylthio-2-benzofuriloxy)phenoxy]acetone, (192) 1-cyano-1-phenylaminocarbonyl-3-[4-(5-ethoxy-2-benzothienyloxy)phenoxy]-2-butanone, (194) 1-cyano-1-(N-ethyl-N-butylthio) aminothiocarbonyl-3-[4-(1-methyl-5-trifluoromethyl-2-benzoindolyloxy)phenoxy]acetone, (196) 1-cyano-1-(N-butoxy-N-methyl) aminothiocarbonyl-3-[4-(1-methyl-5-pentafluoroethyl-2-benzoimidazolyloxy]phenoxy-2-butanone, (198) 1-cyano-1-(5-bromo-2-indolyl)carbonyl-3-[4-(5-chloro-2-benzothiazolyloxy)phenoxy-2-butanone, (200) 1-cyano-1-[1-(3-chloromethyl) piperidinocarbonyl]- 3-[4-(6-chloro-2-benzoxazolyloxy) phenoxy]-2-butanone, (202) 1-cyano-1-(1-piperidinocarbonyl)-3-[4-(5-cyano-oxazolo[5,4-b]-pyridin-2-oxy-2-phenoxy]-2-butanone, (204) 1-cyano-1-(N-cyanomethyl-N-aryl)-aminocarbonyl-3-[4-(thiazolo[5,4-b]-pyrldin-2-oxy) phenoxy]-2-butanone, (206) 1-cyano-1-(N-methyl-N-tosyl)aminothiocarbonyl-3-[4-(6,8-dichloro-2-benzopyridyloxy)phenoxy]-2-butanone, (208) 1-cyano-1-(N-butyl-N-methoxyethyl) aminocarbonyl-4-[4-(5-butyl-1-methyl-2-benzoimidazolyloxy)phenoxy]-2-butanone, (210) 1-cyano-1-(1-pyrrolyl)carbonyl-3-[4-(5-propoxy-2-benzothiazolyloxy)phenoxy]acetone, (212) 1-cyano-1-(1-cycloheptylamino)carbonyl-3-[4-(5-chloro-2-benzoxazolyloxy)phenoxy-butan-2thione, (214) 1-cyano-1-(N-Omethyl-N-methoxymethyl) aminocarbonyl-3-[2,6-dichloro-4 -(oxazolo[5,4-b]-pyridin-2-oxy)phenoxy]-4-butanone, (216) 3-cyano-3-(1-morpholinocarbonyl)-5-[4-(thiazolo [5,4-b]-pyridin-2-oxy)phenoxy]-4-pentanone, (218) 1-cyano-1-(N-cyano-N-ethoxycarbonyl) aminocarbonyl-3-[4-(6-propoxy-2-quinolyloxy)phenoxy-2-butanone, (220) 1-cyano-1-(N-dichlorophenyl-N-methyl) aminocarbonyl-3-[4-(2-quinoxalyloxy)phenoxy]-2-butanone, (222) 1-cyano-1-[1-(3-nitro)indolyl]-carbonyl-3-[4-(6-bromo-2-quinoxalyloxy)phenoxy]-2-butanone, (224) 1-cyano-1-piperidinocarbonyl-3-[4-(6-chloro-2-quinoxalyloxy)phenoxy]acetone, (238) 1-cyano-1-[N-(3,5-dimethylpiperidino)carbonyl]-3-[4-(3-chloro-5-trifluoromethyl-2-pyridyloxy)phenoxy-2-butanone, (245) 1-cyano-1-[N-(1,2,3,4-tetrahydroquinolyl) carbonyl]-3-[4-(3-chloro-5-trifluoromethyl-2-pyridyloxy) phenoxy]-2-butanone, (257) 1-cyano-1-(N-pyrrolyl)carbonyl-3-[4-(2-chloro-4-trifluoromethylphenoxy)phenoxy]-2-butanone, (260) 1-cyano-1-(N-phenyl-N-methyl)aminocarbonyl-3-[4-(2-chloro-4-trifluoromethylphenoxy)phenoxy]-2-butanone, (263) 1-cyano-1-(N,N-dibenzyl)aminocarbonyl-3-[4-(2-chloro-4-trifluoromethylphenoxy)phenoxy]-2-butanone.

The above compounds are particularly industrially easily produced and have excellent herbicidal activity.

The cyanoketone derivative of the formula (1), provided by the present invention, can be structurally identified by measurements of infrared absorption spectrum (IR), mass spectrum (MS) and $^1$H-nuclear magnetic resonance spectrum ($^1$H-NMR) and elemental analysis. Typical patterns thereof are as follows.

(i) In the measurement of the cyanoketone derivative of the formula (1) for infrared absorption spectrum (IR), a characteristic absorption based on the ether bond is observed at 1,180 to 1,230 cm$^{-1}$, and a characteristic absorption based on the cyano group is observed at 2,210 to 2,220 cm$^{-1}$.

(ii) The cyanoketone derivative of the formula (1) is measured for mass spectrum (MS), and its composition formula corresponding to each peak observed (generally, a value of m/e obtained by dividing an ion molecular weight, m, by a number of charge, e) is calculated, whereby the molecular weight of the cyanoketone compound and the bonding mode of each atomic group in the molecule can be determined. That is, when a sample measured has the formula (1), there are generally observed molecular ion peaks (to be abbreviated as "M$^+$" hereinafter) having strength according to an isotopic abundance depending upon the number of halogen atoms contained in the molecule, and the molecular weight of the sample therefore can be determined. Further, the molecular weight generally appears as a mass number of each ion derived from the sample which has been cleaved in positions indicated by dotted lines in the following formula (8)

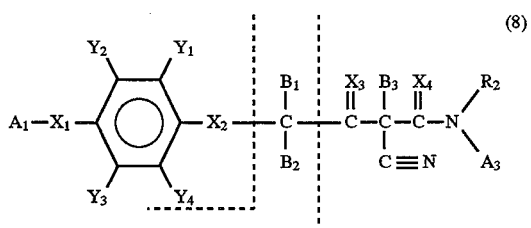

wherein $A_1$, $X_1$, $X_2$, $X_3$, $X_4$, $Y_1$, $Y_2$, $Y_3$, $Y_4$, $B_1$, $B_2$, $B_3$, $A_2$ and $A_3$ are as defined above.

(iii) The bonding mode of hydrogen bonds in the compound of the present invention, represented by the above formula (1), can be determined by measurement of the compound for $^1$H-nuclear magnetic resonance spectrum ($^1$H-NMR). That is, in the measurement of the compound of the formula (1) in a heavy chloroform solvent, a peak of methine substituted with a cyano group often appears at 5.50 to 5.70 ppm as a multiplier since the carbon atom to which the cyano group is bonded is an asymmetric carbon, and protons on the phenyl group show a multiplet at 6.70 to 7.50 ppm.

(iv) The weight of each of carbon, hydrogen and nitrogen (and halogen if contained) is determined by elemental analysis, and then by deducting the total sum of recognized weight percentages of these elements from 100, the weight percentage of oxygen can be determined. Accordingly, the composition formula of the compound can be determined.

The cyanoketone derivative of the present invention generally is a light yellow or yellowish brown viscous body or solid at room temperature under atmospheric pressure.

The cyanoketone derivative of the present invention is well-dissolved in organic solvents such as benzene, ethyl ether, ethyl alcohol, N,N-dimethylformamide, dimethylsulfoxide, chloroform and carbon tetrachloride. However, it is slightly soluble or insoluble in hexane, heptane and water.

The cyanoketone derivative of the formula (1), provided by the present invention, can be produced by any of the following methods (a), (b), (c), (d) and (e).

(a) A method in which a compound of the following formula (9)

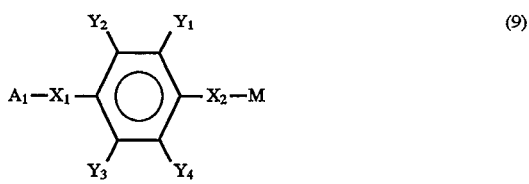

wherein $A_1$, $X_1$, $X_2$, $Y_1$, $Y_2$, $Y_3$ and $Y_4$ are as defined above, and M is a hydrogen atom or an alkali metal,
and a compound of the following formula (10)

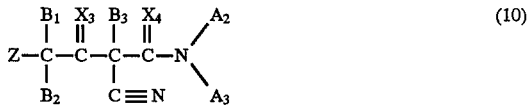

wherein Z is a halogen atom, and $B_1$, $B_2$, $B_3$, $X_3$, $X_4$, $A_2$ and $A_3$ are as defined in the formula (1),
are allowed to react in the presence or absence of a solvent.

(b) A method in which an ester derivative of the following formula (11)

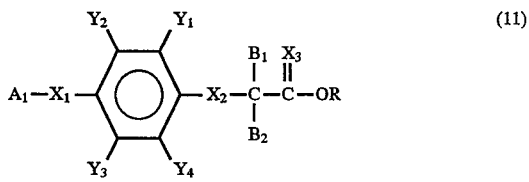

wherein R is an alkyl group, and $A_1$, $X_1$, $X_2$, $X_3$, $Y_1$, $Y_2$, $Y_3$, $Y_4$, $B_1$ and $B_2$ are as defined in the formula (1),
and a cyano derivative of the following formula (12)

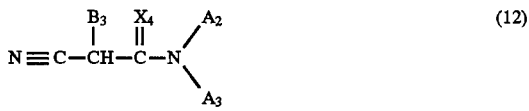

wherein $B_3$, $X_4$, $A_2$ and $A_3$ are as defined in the formula (1),
are allowed to react in the presence or absence of a solvent.

(c) A method in which a compound of the following formula (13)

$$A_1-Z \quad (13)$$

wherein Z is a halogen atom and $A_1$ is as defined in the above formula (1), and a compound of the following formula (14)

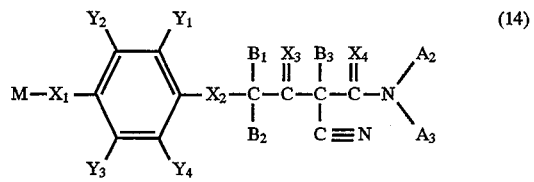

wherein M is a halogen atom or an alkyl metal, $X_1$, $X_2$, $X_3$, $X_4$, $Y_1$, $Y_2$, $Y_3$, $Y_4$, $B_1$, $B_2$, $B_3$, $A_2$ and $A_3$ are as defined in the formula (1),
are allowed to react in the presence or absence of a solvent.

(d) A method in which an acid halide of the following formula (15)

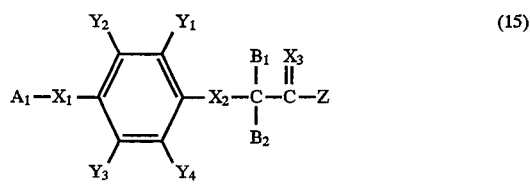

wherein Z is a halogen atom and $A_1$, $B_1$, $B_2$, $X_1$, $X_2$, $X_3$, $Y_1$, $Y_2$, $Y_3$ and $Y_4$ are as defined in the formula (1),
and a compound of the above formula (12) are allowed to react in the presence or absence of a solvent.

(e) A method in which an acid halide of the following formula (16)

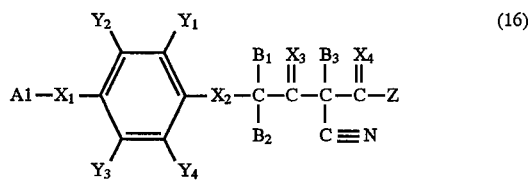

wherein Z is a halogen atom and $A_1$, $B_1$, $B_2$, $B_3$, $X_1$, $X_2$, $X_3$, $X_4$, $Y_1$, $Y_2$, $Y_3$ and $Y_4$ are as defined in the formula (1), and a compound of the following formula (17)

$$A_2-NH-A_3 \quad (17)$$

wherein A2 and A3 are as defined in the formula (1),
are allowed to react in the presence or absence of a solvent.

In the above method (a), the feed molar ratio of the compounds of the formulae (9) and (10) may be properly determined as required. In general, these compounds are used in an equimolar amount or one of these is used in a little excess, for example, in an amount that is greater than the amount of the other by not more than 20%.

In the above method (b), the feed molar ratio of the ester derivative of the formula (11) and the cyano derivative of the formula (12) may be properly determined as required. In general, these compounds are used in an equimolar amount or one of these is used in a little excess, for example, in an amount that is greater than the amount of the other by not more than 20%.

In the above method (c), the feed molar ratio of the compounds of the formulae (13) and (14) may be properly determined as required. In general, these compounds are used in an equimolar amount or one of these is used in a little excess, for example, in an amount that is greater than the amount of the other by not more than 20%.

In the above method (d), the feed molar ratio of the acid halide of the formula (15) and the compound of the formula (12) may be properly determined as required. In general, these compounds are used in an equimolar amount or one of these is used in a little excess, for example, in an amount that is greater than the amount of the other by not more than 20%.

In the above method (e), the feed molar ratio of the acid halide of the formula (16) and the compound of the formula (17) may be properly determined as required. In general, these compounds are used in an equimolar amount or one of these is used in a little excess, for example, in an amount that is greater than the amount of the other by not more than 20%.

The solvent each in the above methods (a) to (c) is not specially limited, and can be selected from known solvents. Typical examples of the solvent include alcohols such as methanol and ethanol; ethers such as diethyl ether, dimethoxyethane, tetrahydrofuran and dioxane; aromatic solvents such as benzene and toluene, chlorine-containing solvents such as methylene chloride, chloroform and carbon tetrachloride; N,N-dimethylformamide; dimethylsulfoxide; and sulfolane.

The solvent each in the above methods (d) and (e) is not specially limited, and can be selected from known solvents. Typical examples of the solvent include ethers such as diethyl ether, dimethoxyethane, tetrahydrofuran and dioxane; aromatic solvents such as benzene and toluene, chlorine-containing solvents such as methylene chloride, chloroform and carbon tetrachloride; N,N-dimethylformamide; dimethylsulfoxide; and sulfolane.

In the methods (a) and (c), when M is hydrogen, the co-presence of a hydrogen halide binding agent is preferred in order to bind the hydrogen halide produced as a by-product. Also in the methods (d) and (e), the co-presence of a hydrogen halide binding agent is preferred in order to bind the hydrogen halide produced as a by-product. The hydrogen halide binding agent is not specially limited, and can be selected from known agents. Typical examples of the hydrogen halide binding agent preferably usable include trialkylamines such as triethylamine, trimethylamine and tripropylamine, pyridine, sodium alcoholate, potassium alcoholate, 1,8-diazabicyclo[5,4,0]-7-undecene, sodium carbonate, potassium carbonate, sodium hydroxide, potassium hydroxide and sodium hydrite.

In the method (b), the condensation agent for removing alcohol from the reaction is not specially limited, and can be selected from known agents. Typical examples of the agent include sodium methylate, potassium methylate, sodium ethylate, potassium ethylate and potassium tert-butylate.

In the methods (a) and (c), examples of the alkali metal, represented by M, in the compounds of the formulae (9) and (14) include sodium, potassium and lithium. Of these metals, sodium and potassium are preferred.

In the methods (a), (c), (d) and (e), examples of the halogen atom, represented by Z, in the compounds of the formulae (10), (13), (15) and (16) include fluorine, chlorine, bromine and iodine.

In the method (b), examples of the alkyl group, represented by R, in the ester derivative of the formula (11) include methyl, ethyl, n-propyl, isopropyl, n-butyl, isobutyl, tert-butyl, pentyl, hexyl, heptyl, octyl, nonyl and decyl. Methyl and ethyl are generally preferably used.

In the methods (a), (b), (c), (d) and (e), the reaction is carried out at a temperature in the range of −30° to 200° C., preferably in the range of 5° to 150° C., for 0.5 to 45 hours, preferably 3 to 24 hours.

The method of isolating the intended product, a cyanoketone derivative, from the reaction system and purifying it is not specially limited, and can be selected from known methods. It is generally preferred to employ a method in which the reaction mixture is added to water, the resultant mixture is subjected to extraction with an organic solvent, and after removing the solvent, the remainder is recrystallized or purified by column chromatography.

A study of the present inventors has showed that the novel cyanoketone derivative of the formula (1), provided by the present invention, has very high herbicidal activity.

According to the present invention, therefore, there is also provided a herbicide containing the cyanoketone derivative of the formula (1) as an effective or active component.

The form for use of the herbicide of the present invention is not specially limited, and can be selected from known forms. For example, it can be used in the form of any one of granules, a dust, an emulsifiable concentrate, a wettable powder, a flowable agent, a tablet, an aerosol and a fuming agent, which are prepared by using an inert solid carrier, a liquid carrier or an emulsification dispersant in combination.

Further, In the preparation of the formulation, there may be incorporated an auxiliary agent such as a wetting agent, a diluent and a surfactant. The herbicide of the present invention can be used in the form of a liquid or a solid to which the above auxiliary agent is properly incorporated. A surfactant is often effective for improvement in the dispersibility of the herbicide in water or an oil.

The above surfactant can be selected from known anionic surfactants, cationic surfactants and nonionic surfactants used for the preparation of general herbicides. Examples of the particularly suitable surfactants include alkylbenzenesulfonic acid, alkylnaphthalenesulfonic acid, fatty acid sulfonate, polyoxyethylene alkylphenyl ether sulfonate, sodium alkylsulfate, sodium lignin sulfonate and polyalkylnaphthalene sulfonate.

Typical examples of the form of the cyanoketone derivative of the formula (1) for use as a herbicide are as follows.

A wettable powder and granules generally contain an inert solid carrier and a surfactant in addition to the active component of the formula (1). The inert solid carrier is generally selected from natural or synthetic inorganic powders. The most preferred are, for example, clays, talc, potassium carbonate, diatomaceous earth and silica. The wettable powder and granules generally contain 1 to 80 parts by weight of the active component, 5 to 98 parts by weight of the inert solid carrier and 1 to 15 parts by weight of the surfactant. Polyvinyl alcohol and sodium carboxymethylcellulose may naturally be incorporated as required.

The emulsifiable concentrate is generally prepared by dissolving the active component and the surfactant in a solvent. The solvent is preferably selected from those which can dissolve the active component. Typical examples of the solvent include xylene, phenoxyethanol, cyclohexane, solvent naphtha, methylnaphthalene and kerosene. The emulsifiable concentrate generally contains 75 to 20 parts by weight of the active component, 10 to 20 parts by weight of the surfactant and 15 to 60 parts by weight of the solvent.

The dust is a product in which the active component is held on a natural or synthetic inorganic powder. The dust is generally prepared by mixing 0.5 to 6 parts by weight of the active component and 99.5 to 94 parts by weight of the inorganic powder.

The flowable agent is a suspension product prepared by suspending the active component insoluble in water, and adding a dispersant to disperse the suspended active component in water. It is the most widely employed embodiment to suspend 20 to 50% by weight of the active component.

The fuming agent is prepared by incorporating a heat generating agent and a heat generation adjuster. The heat generating agent is selected from nitrates, nitrites, guanidine salts and potassium chlorate. The heat generation adjuster is selected from alkali metal salts and potassium nitrates.

The novel cyanoketone derivative of the formula (1) has remarkably high herbicidal activity and is effective against a variety of gramineous weeds. Examples of the weeds against which the herbicidal activity is generally effective include upland soil gramineous weeds such as fall panicum, green foxtail, sorghum, wild oat, Japanese brome, water foxtail, annual bluegrass, barnyardgrass, Johnsongrass, quackgrass, southern crabgrass, goosegrass, Italian ryegrass, burmudagrass and knotgrass.

The cyanoketone derivative of the formula (1) is a novel compound which has high selectivity, i.e., remarkably high herbicidal activity against gramineous weeds and safety for broad-leaved crops. Therefore, It has characteristic features in that it is completely harmless to crops such as soybean, adzuki bean, peanut, sunflower, cotton, etc., even when it is used in a high dosage. When the compound of the formula (1), provided by the invention, is sprayed as a herbicide to gramineous plants, not only the use of it as a soil-applied herbicide is effective, but the use of it as a foliar-applied herbicide is also effective.

In general, the suitable dosage as an active component of the herbicide of the present invention is in the range of 0.05 to 20.0 kg/h, preferably 0.10 to 6.0 kg/h.

The present invention will be explained further in detail hereinafter by reference to Examples. The present invention, however, shall not be limited to these Examples.

Example 1

Preparation of 1-cyano-1-[N,N-(di-3-chlorophenyl)] aminocarbonyl-3-methyl-3-[4-(4-nitrophenoxy)phenoxy]2-butanone (Compound No. 114):

2 Grams of a potassium salt of 4-(4-nitrophenoxy)-phenol and 3.03 g of 1-cyano-1-di(N,N-chlorophenyl)-aminocarbonyl-3-methyl-2-butanone were heated in 50 ml of N,N-dimethylformamide at 100° C. for 6 hours. After the reaction liquid was removed, the reaction mixture was added to water. The mixture was extracted with chloroform, the extract was concentrated. The residue was separated and purified by column chromatography to give 2.73 g of a compound No. 144 which was a pale yellow solid (melting point 186°–188° C.). The yield was 61.1%. The compound No. 144 was analyzed, and the results are shown in Tables 1 to 18.

Example 2

Preparation of 1-cyano-1-piperidylcarbonyl-3-[4-(2-chloro-4-trifluoromethylphenoxy)phenoxy]-2-butanone (Compound No. 100):

To a solution of 0.62 g of metal sodium in 50 ml of ethanol were added 4.20 g of ethyl 2-[-(2-chloro-5-trifluoromethyl-2-phenoxy)phenoxy]propionate and 1.62 g of 1-cyanoacetylpiperidine, and the mixture was refluxed under heat for 4 hours. The reaction liquid was removed, and the residue was added to water. The mixture was acidified with hydrochloric acid, and then extracted with chloroform, followed by concentrating the extract. The residue was separated and purified by column chromatography to obtain 2.52 g of a compound No. 100 which was a pale yellow viscous substance. The yield was 47.3%. The compound No. 100 was analyzed, and the results are shown in Tables 1 to 18.

Example 3

Preparation of 1-cyano-1-(1-pyrrolidyl)carbonyl-3-[4-(3-chloro-5-trifluoromethyl-2-pyridyloxy)phenoxy]-2-butanone (Compound No. 154):

2.15 Grams of 2,3-dichloro-5-trifluoromethylpyridine, 3.02 g of 1-cyano-1-(pyrrolidyl)carbonyl-3-(4-hydroxyphenoxy)-2-butanone and 1.66 g of potassium carbonate were refluxed in 50 ml of acetonitrile under heat at 80° C. for 3 hours. The reaction liquid was filtered, and the filtrate was removed. The residue was separated and purified by column chromatography to obtain 4.00 g of a compound No. 154 which was a pale yellow viscous substance. The yield was 83.2%. The compound No. 154 was analyzed, and the results are shown in Tables 1 to 18.

Example 4

Preparation of 1-cyano-1-(1-piperidyl)carbonyl-3-[4-(3-chloro-5-trifluoromethyl-2-pyridyloxy)-phenoxy]-2-butanone (Compounds No. 150):

A solution of 3.00 g of 2-[4-(3-chloro-5-trifluoromethyl-2-pyridyl)phenoxy]propionyl chloride in 20 ml of benzene was added dropwise to a solution containing 1.20 g of 1-cyanoacetylpiperidine, 1.44 of DBU and 30 ml of benzene. Then the mixture was refluxed under heat at 90° C. for 5 hours. After the reaction liquid was removed, the mixture was extracted with chloroform, and the extract was concentrated. The residue was separated and purified by column chromatography to obtain 2.08 g of a compound No. 150 which was a pale yellow viscous substance. The yield was 53.1%. The compound No. 150 was analyzed, and the results are shown in Tables 1 to 18.

Example 5

Preparation of 1-cyano-1-(N-propoxy-N-methyl) aminocarbonyl-3-[4-(1-methyl-5 -pentatrifluoroethyl-2-benzolmidazolyloxy)phenoxy]-2-butanone (Compounds No. 196):

A solution of 3.00 g of 4-[4-(1-methyl-5-pentafluoroethyl-2-benzoimidazoyloxy)phenoxy]-2-cyano-3-oxypentanoyl chloride in 20 ml of dimethoxyethane was added dropwise to a solution containing 0.60 g of N-propoxy-N-methylamine, 0.81 g of triethylamine and 30 ml of dimethylethane. Then, the mixture was stirred at room temperature for 6 hours. After the reaction liquid was removed, the mixture was extracted with chloroform, and the extract was concentrated. The residue was separated and purified by column chromatography to obtain 2.82 g of a compound No. 196 which was a pale yellow viscous substance. The yield was 84.2%. The compound No. 196 was analyzed, and the results are shown in Tables 1 to 18.

Example 6

Preparation of R- and S-enantiomers of 1-cyano-1-(1-piperidyl)carbonyl-3-[4-(3-chloro-5-trifluoromethyl-2-pyridyloxy)phenoxy]-2-butanone (Compound Nos. 150(a) and 150(b):

The compounds No. 150 obtained in Example 4 was separated into R- and S-enantiomers (compounds Nos. 150 (a) and 150(b)) using a column for separation of optical isomers (OD-1, supplied by Daicel Chemical Industries, Ltd). A specific rotation $[\alpha]_D$ of the R-isomer was 22.1°, and that of S-isomer was −20.8°. The R- and S-isomers were with respect to other items, and the results showed the same values as those of the compound. No.150 shown in Tables 1 to 18.

Example 7

Compounds Nos. 122, 128, 142 and 160 were produced in the same manner as in Example 1. Compounds 146, 184, 186, 188, 200, 210 and 216 were produced in the same manner as in Example 2. Compounds Nos. 108, 134, 138, 166, 174, 176, 198, 222, 238, 245 and 246 were produced in the same manner as in Example 3. Compounds Nos. 102, 104, 116, 118, 132, 140, 162, 164, 168, 170, 180, 190, 202, 212, 224, 248, 257, 260 and 263 were produced In the same manner as in Example 4. Compounds Nos. 106, 110, 112, 120, 124, 126, 130, 136, 144, 148, 152, 156, 158, 172, 178, 182, 192, 194, 204, 206, 208, 214, 218 and 220 were produced in the same manner as in Example 5. The obtained compounds were analyzed, and the results are shown in Tables 1 to 18. In these tables, infrared spectra only show characteristic absorptions ascribed to an ether bond and a cyano group which were obtained from the measurements, and mass spectra show molecular ion peaks ($M^+$) and fragment peaks cleaved in positions shown in the formula (7) which were common among all the compounds, these peaks being obtained from the measurements.

In the column of "Elemental analysis" in Tables 1 to 18, the upper row values show the found and the lower row values, the calculated.

TABLE 1

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C, CN) | Elemental analysis C / H / N | ¹H-NMR |
|---|---|---|---|---|---|---|---|---|---|---|---|---|---|---|---|---|---|
| 100 | 2-Cl, 4-CF₃-phenyl | CH₃ | H | H | O | O | O | O | H | H | H | H | piperidino | 494(M⁺) 315 287 | 1180 2210 | 58.11 4.58 5.55 / 58.25 4.48 5.66 | 1.20–2.14(m, 9H) 3.42–3.70(m, 4H) 4.32–5.42(m, 2H) 7.10–7.48(m, 7H) |
| 102 | 4-Br-phenyl | CH₃ | H | H | O | O | O | O | H | H | H | H | pyrrolidino | 456(M⁺) 291 263 | 1180 2210 | 57.56 4.76 6.10 / 57.78 4.63 6.13 | 1.12–2.48(m, 7H) 2.38–2.59(m, 4H) 4.28–5.55(m, 2H) 6.89–7.40(m, 8H) |
| 104 | phenyl | CH₃ | H | H | O | O | O | O | H | Br | Br | H | N-methylpiperazino | 563(M⁺) 369 341 | 1190 2210 | 48.78 4.10 7.35 / 48.87 4.10 7.43 | 1.27–1.80(m, 3H) 2.20–2.47(m, 7H) 2.70–3.00(m, 4H) 4.32–5.48(m, 2H) 6.95–7.38(m, 7H) |
| 106 | 1-naphthyl | CH₃ | H | H | O | O | O | O | H | H | H | H | 2,5-dihydropyrrol-1-yl | 426(M⁺) 263 235 | 1180 2220 | 73.30 5.21 6.56 / 73.22 5.20 6.57 | 1.26–1.57(m, 3H) 3.72(s, 4H) 4.27–5.60(m, 2H) 5.82(s, 2H) 7.00–8.24(m, 11H) |

TABLE 2

| Compound No. | A₁ | B₁ | B₂ | B₃ | X₁ | X₂ | X₃ | X₄ | Y₁ | Y₂ | Y₃ | Y₄ | $-N\begin{smallmatrix}A_2\\A_3\end{smallmatrix}$ | MASS | i.r.(cm⁻¹) (C—O—C,CN) | Elemental analysis C / H / N | ¹H-NMR |
|---|---|---|---|---|---|---|---|---|---|---|---|---|---|---|---|---|---|
| 108 | naphthyl | H | H | H | O | O | O | O | H | H | H | H | morpholino | 430(M⁺) 249 235 | 1190 2220 | 69.91 5.02 6.59 / 69.76 5.15 6.51 | 2.82–3.04(m, 4H) 3.61–3.82(m, 4H) 4.78(s, 2H) 5.64(s, 1H) 7.05–8.21(m, 11H) |
| 110 | 5-methyl-2-thienyl | CH₃ | H | H | O | O | O | O | H | H | H | H | —N(CO₂C₄H₉)(CH₃) | 458(M⁺) 233 205 | 1180 2210 | 60.44 5.58 6.13 / 60.25 5.72 6.11 | 0.81–1.93(m, 10H) 2.43(s, 3H) 2.62(s, 3H) 4.02–5.56(m, 4H) 7.03–7.81(m, 6H) |
| 112 | 2-furyl | CH₃ | H | H | O | O | O | O | H | H | H | H | —N(CH₃)(CH₃) | 398(M⁺) 203 175 | 1180 2210 | 66.20 6.65 6.88 / 66.32 6.58 7.03 | 0.75–1.82(m, 13H) 2.50–2.93(t, 6H) 4.25–5.60(m, 2H) 7.05–7.62(m, 7H) |
| 114 | 4-nitrophenyl | CH₃ | CH₃ | H | O | O | O | O | H | H | H | H | —N(2-chlorophenyl)(2-chlorophenyl) | 603(M⁺) 272 230 | 1180 2220 | 61.81 3.76 7.12 / 61.60 3.84 6.95 | 1.48(s, 3H) 1.60(s, 3H) 6.04(s, 1H) 7.00–7.45(m, 16H) |

TABLE 3

| Compound No. | A₁ | B₁ | B₂ | B₃ | X₁ | X₂ | X₃ | X₄ | Y₁ | Y₂ | Y₃ | Y₄ | $-N\begin{smallmatrix}A_2\\A_3\end{smallmatrix}$ | MASS | i.r.(cm⁻¹) (C—O—C,CN) | Elemental analysis C / H / N | ¹H-NMR |
|---|---|---|---|---|---|---|---|---|---|---|---|---|---|---|---|---|---|
| 116 | H₃CS-naphthyl | H | H | H | S | O | O | O | H | H | H | H | N-piperidine-N-CH₃ | 505(M⁺) 311 297 | 1170 2210 | 63.98 5.52 8.12 / 64.13 5.38 8.31 | 2.20–2.54(m, 10H) 2.74–3.03(m, 4H) 4.70(s, 2H) 7.04–8.30(m, 10H) |
| 118 | OCH₃-thienyl | CH₃ | H | H | H | O | O | O | H | H | H | H | N-pyrrolidine | 414(M⁺) 249 221 | 1170 2220 | 60.71 5.40 6.64 / 60.85 5.35 6.76 | 1.21–2.00(m, 7H) 2.32–2.54(m, 4H) 3.48(s, 3H) 4.22–5.48(m, 2H) 7.03–7.56(m, 6H) |
| 120 | F-furyl | H | H | H | H | O | O | O | Cl | H | H | Cl | N-morpholine | 456(M⁺) 275 261 | 1180 2210 | 50.20 3.15 6.28 / 49.91 3.31 6.13 | 2.78–3.00(m, 4H) 3.63–3.84(m, 4H) 4.70(s, 2H) 5.68(s, 1H) 7.00–7.68(m, 4H) |
| 122 | CO₂CH₃-N-CH₃-pyrrolyl | CH₃ | H | H | H | O | O | O | H | H | H | H | N-(3-CH₃-pyrrolyl) | 449(M⁺) 274 246 | 1170 2210 | 63.98 5.22 9.33 / 64.13 5.16 9.35 | 1.16–1.83(m, 3H) 2.48(s, 3H) 3.48(s, 3H) 3.52(s, 3H) 4.34–5.47(m 2H) 7.00–7.88(m, 9H) |

TABLE 4

| Compound No. | A₁ | B₁ | B₂ | B₃ | X₁ | X₂ | X₃ | X₄ | Y₁ | Y₂ | Y₃ | Y₄ | −N(A₂)(A₃) | MASS | i.r.(cm⁻¹) (C—O—C,CN) | Elemental analysis C H N | ¹H-NMR |
|---|---|---|---|---|---|---|---|---|---|---|---|---|---|---|---|---|---|
| 124 | ![pyrazole-CH₂-] | CH₃ | H | H | O | O | O | O | H | H | H | H | −N(CH₂SC₂H₅)(CH₃) | 402(M⁺) 203 175 | 1180 2220 | 56.86 5.52 14.04 / 56.70 5.51 13.92 | 1.11–1.83(m, 6H) 2.10(s, 3H) 2.22–2.74(m, 5H) 4.40–5.62(m, 2H) 7.02–7.42(m, 6H) 12.40(bs, 1H) |
| 126 | ![pyrazole-CH₂-] | CH₃ | H | H | O | O | O | O | H | H | H | H | −N(CH₂-tetrahydrofuran)(H) | 398(M⁺) 203 175 | 1190 2220 | 60.46 5.40 14.20 / 60.29 5.57 14.06 | 1.26–2.16(m, 7H) 3.41(d, 2H) 3.94–5.44(m, 5H) 6.70–7.76(m, 6H) 8.82(bs, 1H) 13.10(bs, 1H) |
| 128 | H₅C₂O₂C-(furan)- | CH₃ | H | H | O | O | O | O | H | H | H | H | −N(pyrrole) | 438(M⁺) 276 248 | 1200 2220 | 57.50 4.20 12.90 / 57.53 4.14 12.78 | 1.20–1.88(m, 6H) 4.20–5.62(m, 4H) 7.02–7.62(m, 8H) |
| 130 | H₉C₄O₂CH₂C-(thiophene)- | CH₃ | H | H | O | O | O | O | H | H | H | H | −N(5-chlorobenzofuran-2-yl)(CH₃) | 609(M⁺) 334 306 | 1190 2210 | 58.85 4.80 6.80 / 59.06 4.63 6.89 | 1.13–1.92(m, 10H) 2.42(s, 3H) 3.64(s, 2H) 4.08–5.47(m, 4H) 6.15(s, 1H) 7.00–7.40(m, 7H) 8.42(s, 1H) |

TABLE 5
| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C,CN) | Elemental analysis C H N | ¹H-NMR |
|---|---|---|---|---|---|---|---|---|---|---|---|---|---|---|---|---|---|
| 132 | 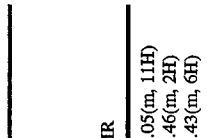 | CH₃ | H | H | O | O | O | O | H | H | H | H | 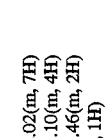 | 427(M⁺) 220 192 | 1180 2210 | 61.76 5.77 9.95<br>61.81 5.89 9.83 | 0.62–3.05(m, 11H)<br>4.44–5.46(m, 2H)<br>7.00–8.43(m, 6H) |
| 134 | 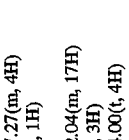 | CH₃ | H | H | O | O | O | O | H | H | H | H | 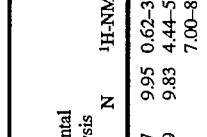 | 369(M⁺) 204 176 | 1170 2220 | 61.62 5.25 11.30<br>61.78 5.19 11.38 | 1.23–2.02(m, 7H)<br>2.60–3.10(m, 4H)<br>4.52–5.46(m, 2H)<br>6.62(d, 1H)<br>7.00–7.27(m, 4H)<br>8.42(d, 1H) |
| 136 | 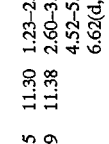 | CH₃ | H | H | O | O | S | O | H | H | H | H | 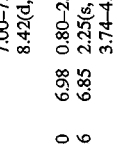 | 613(M⁺) 342 314 | 1190 2210 | 49.03 5.20 6.98<br>48.94 5.26 6.85 | 0.80–2.04(m, 17H)<br>2.25(s, 3H)<br>3.74–4.00(t, 4H)<br>4.40–5.38(m, 2H)<br>5.82(d, 1H)<br>7.00–7.44(m, 5H) |
| 138 | 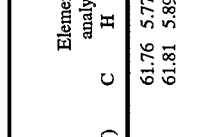 | CH₃ | H | H | O | O | O | O | H | H | H | H | 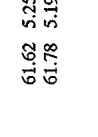 | 466(M⁺) 259 217 | 1190 2220 | 66.74 7.34 11.89<br>66.93 7.35 12.01 | 0.60–3.22(m, 24H)<br>3.48(s, 3H)<br>4.30–5.42(m, 2H)<br>6.96–7.24(m, 5H) |

TABLE 6

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C,CN) | Elemental analysis C | H | N | ¹H-NMR |
|---|---|---|---|---|---|---|---|---|---|---|---|---|---|---|---|---|---|---|---|
| 140 | ![A1: N-N(CH3) ring] | CH₃ | H | H | O | O | O | O | CH₃ | H | H | H | -NH-C₆H₄(p-NO₂) with CH₃ | 477(M⁺) 231 203 | 1180 2220 | 60.10 60.37 | 4.90 4.86 | 14.65 14.67 | 1.12–1.83(m, 3H) 2.21(s, 3H) 2.42(s, 3H) 4.00(s, 3H) 4.48–5.39(m, 2H) 6.12(d, 2H) 7.10–7.56(m, 8H) |
| 142 | ![A1: N-O ring] | CH₃ | H | H | O | O | O | O | H | H | H | H | pyrrolidinyl | 368(M⁺) 204 176 | 1180 2210 | 58.76 58.69 | 4.50 4.38 | 15.17 15.21 | 1.22–1.92(m, 3H) 2.46(bs, 4H) 4.32–5.40(m, 2H) 7.12–7.82(m, 7H) |
| 144 | ![A1: H5C2S-N=S ring] | CH₃ | H | H | O | S | S | O | H | H | H | H | -NH-C₆H₄(p-CN) with CH₂CO₂CH₃ | 596(M⁺) 296 268 | 1170 2210 | 54.17 54.34 | 4.16 4.05 | 9.28 9.39 | 1.12–1.88(m, 6H) 3.00(q, 2H) 3.82(s, 3H) 3.86(s, 3H) 4.46–5.42(m, 2H) 7.00–7.46(m, 9H) |
| 146 | ![A1: N=N-S ring] | CH₃ | H | CH₃ | O | O | O | O | H | H | H | H | morpholino | 415(M⁺) 220 192 | 1180 2220 | 58.05 57.82 | 5.02 5.10 | 10.13 10.12 | 1.02–1.96(m, 6H) 2.78–3.00(m, 4H) 3.52–3.78(m, 4H) 5.42–5.58(m, 1H) 7.12–7.69(m, 6H) |

TABLE 7

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C,CN) | Elemental analysis C | H | N | ¹H-NMR |
|---|---|---|---|---|---|---|---|---|---|---|---|---|---|---|---|---|---|---|---|
| 148 | (isoxazole group) | H | H | H | O | O | O | O | H | H | H | H | —N(H)(CH₂-C₆H₅-CH₂Cl) | 425(M⁺) 190 176 | 1180 2210 | 59.01 59.23 | 3.79 3.79 | 9.65 9.87 | 4.68(s, 2H) 5.02(s, 2H) 6.98–7.64(m, 11H) |
| 150 | (3-Cl, 5-CF₃-pyridyl) | CH₃ | H | H | O | O | O | O | H | H | H | H | piperidino | 495(M⁺) 316 288 | 1190 2220 | 55.76 55.71 | 4.26 4.27 | 8.60 8.47 | 1.21–1.98(m, 9H) 2.32–2.54(m, 4H) 4.40–5.38(m, 2H) 7.12–7.78(m, 6H) |
| 152 | (3,5-diCl-pyridyl) | CH₃ | H | H | O | O | O | O | H | H | H | H | —N=C(CH₃)—O—C₆H₃(Cl) | 558(M⁺) 282 254 | 1190 2220 | 53.52 53.64 | 3.00 3.06 | 10.04 10.01 | 1.03–1.82(m, 3H) 2.25(s, 3H) 4.37–5.40(m, 2H) 6.88–7.64(m, 9H) |
| 154 | (3-Cl, 5-CF₃-pyridyl) | CH₃ | H | H | O | O | O | O | H | H | H | H | pyrrolidino | 481(M⁺) 316 288 | 1190 2220 | 54.67 54.84 | 4.05 3.97 | 8.66 8.72 | 1.06–2.10(m, 7H) 2.35–2.84(m, 4H) 4.37–5.28(m, 2H) 7.05–7.86(m, 6H) |

TABLE 8

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C, CN) | Elemental analysis C | H | N | ¹H-NMR |
|---|---|---|---|---|---|---|---|---|---|---|---|---|---|---|---|---|---|---|---|
| 156 | 4-CF₃-pyridin-2-yl | CH₃ | H | H | O | O | O | O | H | H | H | H | -NH-C(=S)-NH-(2-thiophenyl-phenyl) | 526(M⁺) 282 254 | 1180 2210 | 57.01 57.03 | 3.40 3.26 | 10.69 10.64 | 1.12–1.80(m, 3H) 4.36–5.40(m, 2H) 6.88–7.74(m, 7H) 8.75(bs, 1H) |
| 158 | pyrazin-2-yl | H | H | H | O | O | O | O | H | H | H | H | pyrazolidin-1-yl | 367(M⁺) 201 187 | 1170 2210 | 58.59 58.85 | 4.56 4.66 | 19.03 19.07 | 2.00–2.32(m, 3H) 2.40–3.00(m, 4H) 4.70(s, 2H) 5.62(s, 1H) 7.05–7.30(m, 4H) 8.48–8.72(m, 3H) |
| 160 | 6-methyl-2H-pyran-2-yl | H | H | H | O | O | O | O | H | H | H | H | azepan-1-yl | 424(M⁺) 245 231 | 1180 2220 | 67.82 67.91 | 6.46 6.65 | 6.72 6.60 | 0.82–2.00(m, 13H) 2.24–2.68(m, 6H) 4.66(s, 2H) 5.58(s, 1H) 6.84–7.60(m, 6H) |
| 162 | 5-cyano-pyridin-2-yl | C₂H₅ | H | H | O | O | O | O | H | H | H | H | pyrrolidin-1-yl | 418(M⁺) 253 211 | 1190 2220 | 65.89 66.02 | 5.46 5.30 | 13.19 13.39 | 0.96–2.00(m, 7H) 2.20–2.46(m, 6H) 4.40–5.31(m, 2H) 7.08–7.88(m, 7H) |

TABLE 9

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C,CN) | Elemental analysis C | H | N | ¹H-NMR |
|---|---|---|---|---|---|---|---|---|---|---|---|---|---|---|---|---|---|---|---|
| 164 | 3-pyridyl | CH₃ | H | H | O | O | O | O | H | H | H | H | 2-(N-ethyl)amino-4,6-dimethylpyrimidine | 460(M⁺) 215 187 | 1170 2220 | 62.82 62.60 | 5.31 5.25 | 18.11 18.25 | 1.00–1.86(m, 6H) 2.24–2.60(m, 8H) 4.26–5.30(m, 2H) 7.04–7.36(m, 5H) 8.52–8.66(m, 3H) |
| 166 | 2-methyl-5,6-dihydro-2H-pyranyl | H | H | H | O | O | O | O | Cl | H | H | Cl | pyrrol-1-yl | 433(M⁺) 271 257 | 1180 2210 | 52.59 52.55 | 3.22 3.02 | 9.77 9.68 | 1.26–1.44(m, 2H) 4.70(s, 2H) 5.50(s, 1H) 7.02–7.80(m, 8H) |
| 168 | 2-methyl-6-methoxy-thiopyranyl | CH₃ | H | H | O | O | O | O | H | H | H | H | piperidin-1-yl | 442(M⁺) 263 235 | 1180 2220 | 62.61 62.42 | 6.05 5.92 | 6.52 6.33 | 1.10–1.98(m, 11H) 2.20–2.64(m, 4H) 3.40(s, 3H) 7.00–7.48(m, 6H) |
| 170 | 2-methyl-4,6-dimethoxy-pyrimidinyl | CH₃ | H | H | O | O | O | O | H | H | H | H | piperidin-1-yl | 454(M⁺) 275 247 | 1180 2220 | 60.90 60.78 | 5.56 5.77 | 12.13 12.33 | 1.06–1.90(m, 9H) 2.28–2.66(m, 4H) 4.06(s, 6H) 4.35–5.26(m, 2H) 6.88–7.49(m, 5H) |

TABLE 10

| Compound No. | A₁ | B₁ | B₂ | B₃ | X₁ | X₂ | X₃ | X₄ | Y₁ | Y₂ | Y₃ | Y₄ | $-N\begin{matrix}A_2\\A_3\end{matrix}$ | MASS | i.r.(cm⁻¹) (C—O—C,CN) | Elemental analysis C H N | ¹H-NMR |
|---|---|---|---|---|---|---|---|---|---|---|---|---|---|---|---|---|---|
| 172 | (pyrimidine with H₇C₃ groups) | CH₃ | H | H | O | O | O | O | H | H | H | H | -N(CH₂OC₂H₅)(C₄H₉) | 525(M⁺) 300 272 | 1200 2210 | 63.89 7.44 13.21<br>63.98 7.48 13.32 | 1.02-2.06(m, 23H)<br>2.42-3.42(m, 10H)<br>4.42-5.24(m, 2H)<br>7.00-7.32(m, 4H) |
| 174 | cyclohexyl | CH₃ | H | H | O | O | O | O | F | F | F | F | -N(pyrazole, N=N) | 454(M⁺) 291 263 | 1190 2210 | 53.02 4.10 12.33<br>52.87 3.99 12.33 | 0.56-2.38(m, 14H)<br>4.66-5.40(m, 2H)<br>7.26(bs, 2H) |
| 176 | 5-bromo-2-furyl-vinyl | CH₃ | H | H | O | O | O | O | H | H | H | H | -N(imidazole) | 494(M⁺) 331 303 | 1190 2220 | 53.29 3.25 11.16<br>53.35 3.05 11.31 | 1.11-1.76(m, 3H)<br>4.65-5.44(m, 2H)<br>6.86-7.48(m, 8H)<br>8.06(bs, 2H) |
| 178 | 2-methylbenzothiophene | CH₂Cl | CH₃ | H | O | O | O | O | H | H | H | H | -N(CH₃)(5-methylfuran-2-yl) | 508(M⁺) 317 289 | 1180 2220 | 61.46 4.36 5.67<br>61.35 4.16 5.50 | 1.05-1.78(m, 3H)<br>2.20(s, 3H)<br>4.60-5.44(m, 4H)<br>7.06-7.60(m, 11H) |

TABLE 11

| Compound No. | A₁ | B₁ | B₂ | B₃ | X₁ | X₂ | X₃ | X₄ | Y₁ | Y₂ | Y₃ | Y₄ | $-N\genfrac{}{}{0pt}{}{A_2}{A_3}$ | MASS | i.r.(cm⁻¹) (C—O—C,CN) | Elemental analysis C / H / N | ¹H-NMR |
|---|---|---|---|---|---|---|---|---|---|---|---|---|---|---|---|---|---|
| 180 | (1,2-dimethylindol-3-yl, N-CH₃) | CH₃ | H | H | O | O | O | O | H | H | H | H | (3,5-dimethylpiperidin-1-yl) | 487(M⁺) 280 252 | 1180 2220 | 71.57 6.88 8.55 / 71.43 6.82 8.62 | 0.72–3.12(m, 23H) 4.04(s, 3H) 4.60–5.38(m, 2H) 7.02–7.48(m, 8H) |
| 182 | (6-methyl-2-ethylthiophen-3-yl) | CH₃ | H | H | O | O | O | O | H | H | H | H | (5-methylthiopyridin-2-yl)(N-C₃H₇) | 537(M⁺) 261 233 | 1190 2210 | 62.39 5.78 7.78 / 62.54 5.81 7.82 | 0.80–2.05(m, 13H) 2.63–2.94(m, 7H) 4.60–5.36(m, 2H) 7.12–7.83(m, 9H) |
| 184 | (2,6-dimethylpyrimidin-4-yl) | CH₃ | H | H | O | O | O | O | H | H | H | H | (4-methylpiperazin-1-yl) | 437(M⁺) 243 215 | 1180 2210 | 63.29 6.25 16.14 / 63.14 6.22 16.01 | 1.03–1.72(m, 3H) 2.08–3.12(m, 17H) 4.63–5.40(m, 2H) 7.03–7.28(m, 5H) |
| 186 | (2-methylpyrazin-3-yl) | CH₃ | H | H | O | O | O | O | H | H | H | H | N(4-methoxycarbonylphenyl)(phenyl) | 537(M⁺) 216 188 | 1170 2210 | 64.67 4.40 13.03 / 64.80 4.31 13.03 | 1.17–1.83(m, 3H) 4.02(s, 3H) 4.36–5.30(m, 2H) 7.01–7.48(m, 13H) 9.24(bs, 2H) |

TABLE 12

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C,CN) | Elemental analysis C H N | ¹H-NMR |
|---|---|---|---|---|---|---|---|---|---|---|---|---|---|---|---|---|---|
| 188 | cyclohexyl | H | H | H | O | O | O | O | H | Cl | Cl | H | (pyrrolidinyl) | 438(M⁺) 273 259 | 1190 2210 | 57.28 5.45 6.20 / 57.41 5.51 6.38 | 0.62–2.46(m, 19H) 4.68(s, 2H) 5.57(s, 1H) 7.12(bs, 2H) |
| 190 | H₇C₃S-phenyl | H | H | H | O | O | O | O | H | H | H | H | (N-methylpiperazinyl) | 507(M⁺) 313 299 | 1190 2210 | 62.67 5.82 8.12 / 63.89 5.76 8.28 | 0.94–1.90(m, 5H) 2.12–3.10(m, 13H) 4.72(s, 2H) 5.50(s, 1H) 7.00–7.48(m, 8H) |
| 192 | H₅C₂O-phenyl | CH₃ | H | H | O | O | O | O | H | H | H | H | -NH-phenyl | 500(M⁺) 313 285 | 1180 2210 | 67.10 4.88 5.37 / 67.18 4.83 5.60 | 1.08–1.88(m, 6H) 4.02(q, 2H) 4.36–5.28(m, 2H) 6.98–7.64(m, 13H) 8.82(bs, 1H) |
| 194 | F₃C-(N-CH₃-indolyl) | H | H | H | O | O | O | S | H | H | H | H | -N(SC₃H₇)(C₂H₅) | 549(M⁺) 320 306 | 1180 2210 | 56.68 4.56 7.56 / 56.82 4.77 7.65 | 0.82–2.03(m, 8H) 2.33–2.96(m, 4H) 3.52(s, 3H) 4.69(s, 2H) 5.60(s, 1H) 6.32(s, 1H) 7.03–7.52(m, 7H) |

TABLE 13

| Compound No. | $A_1$ | $B_1$ | $B_2$ | $B_3$ | $X_1$ | $X_2$ | $X_3$ | $X_4$ | $Y_1$ | $Y_2$ | $Y_3$ | $Y_4$ | $-N\begin{smallmatrix}A_2\\A_3\end{smallmatrix}$ | MASS | i.r.(cm$^{-1}$) (C—O—C,CN) | Elemental analysis C H N | $^1$H-NMR |
|---|---|---|---|---|---|---|---|---|---|---|---|---|---|---|---|---|---|
| 196 | F$_5$C$_2$-⟨phenyl with N-CH$_3$ substituent⟩ | CH$_3$ | H | H | O | O | O | O | H | H | H | H | -N(OC$_3$H$_7$)(CH$_3$) | 568(M$^+$) 385 357 | 1190 2210 | 54.98 4.50 9.76 / 54.93 4.43 9.86 | 1.10–1.84(m, 8H) 2.28(s, 3H) 3.50(s, 3H) 4.40–5.34(m, 2H) 7.10–7.52(m, 7H) |
| 198 | Cl-⟨phenyl, S⟩ | CH$_3$ | H | H | O | O | O | O | H | H | H | H | 5-bromoindol-1-yl | 593(M$^+$) 304 276 | 1200 2220 | 54.36 2.76 6.97 / 54.51 2.88 7.06 | 1.08–1.76(m, 3H) 4.32–5.20(m, 2H) 6.95–7.78(m, 12H) |
| 200 | Cl-⟨phenyl, O⟩ | CH$_3$ | H | H | O | O | O | O | H | H | H | H | 3-(chloromethyl)piperidin-1-yl | 515(M$^+$) 288 260 | 1180 2210 | 57.94 4.58 8.00 / 58.15 4.49 8.14 | 0.90–3.82(m, 14H) 4.44–5.30(m, 2H) 7.03–7.44(m, 7H) |
| 202 | NC-⟨pyridyl, O⟩ | CH$_3$ | H | H | O | O | O | O | H | H | H | H | piperidin-1-yl | 459(M$^+$) 280 252 | 1180 2210 | 62.70 4.55 15.02 / 62.74 4.61 15.24 | 1.07–1.98(m, 9H) 2.21–2.53(m, 4H) 4.38–5.27(m, 2H) 7.12–8.21(m, 6H) |

TABLE 14

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C,CN) | Elemental analysis C | H | N | ¹H-NMR |
|---|---|---|---|---|---|---|---|---|---|---|---|---|---|---|---|---|---|---|---|
| 204 | pyridyl-thiazole (2-position) | CH₃ | H | H | O | O | O | O | H | H | H | H | -N(CH₂CH=CH₂)(CH₂CN) | 461(M⁺) 271 243 | 1190 2210 | 59.76 59.86 | 4.20 4.15 | 15.11 15.18 | 1.08–1.74(m, 3H) 3.21–3.44(m, 2H) 4.12(s, 2H) 4.38–6.32(m, 5H) 7.09–8.00(m, 7H) |
| 206 | 5,7-dichloro-2-methyl-indolizine | CH₃ | H | H | O | O | O | O | H | H | H | H | -N(p-tolyl)(CH₃) | 547(M⁺) 332 304 | 1170 2220 | 63.33 63.51 | 4.30 4.23 | 7.67 7.66 | 1.03–1.72(m, 3H) 2.24(s, 3H) 2.31(s, 3H) 4.31–5.28(m, 2H) 7.08–8.06(m, 12H) |
| 208 | H₉C₄-phenyl with N—CH₃ and isopropylidene-amino | C₂H₅ | H | H | O | O | O | O | H | H | H | H | -N(C₂H₄OCH₃)(C₃H₇) | 549(M⁺) 337 295 | 1170 2210 | 67.80 67.74 | 7.58 7.52 | 10.00 10.19 | 0.74–2.00(m, 15H) 2.28–3.24(m, 14H) 3.58(s, 3H) 4.31–5.28(m, 2H) 7.03–7.49(m, 7H) |
| 210 | H₃CO-phenyl-CN with S and isopropylidene-amino | H | H | H | O | O | O | O | CH₃ | H | H | H | pyrrolidinyl | 493(M⁺) 328 314 | 1180 2220 | 63.09 63.27 | 5.55 5.51 | 8.44 8.51 | 0.94–1.84(m, 9H) 2.20–2.62(m, 7H) 3.81(t, 2H) 4.68(s, 2H) 5.58(s, 1H) 6.88–7.89(m, 6H) |

TABLE 15

| Compound No. | $A_1$ | $B_1$ | $B_2$ | $B_3$ | $X_1$ | $X_2$ | $X_3$ | $X_4$ | $Y_1$ | $Y_2$ | $Y_3$ | $Y_4$ | $-N\begin{smallmatrix}A_2\\A_3\end{smallmatrix}$ | MASS | i.r.(cm$^{-1}$) (C—O—C,CN) | Elemental analysis C H N | $^1$H-NMR |
|---|---|---|---|---|---|---|---|---|---|---|---|---|---|---|---|---|---|
| 212 |  | CH$_3$ | H | H | O | O | S | O | H | H | H | H |  | 511(M$^+$) 288 260 | 1180 2210 | 60.85 5.17 8.09<br>60.99 5.12 8.21 | 1.16–1.84(m, 13H)<br>2.63–2.98(m, 4H)<br>4.40–5.36(m, 2H)<br>7.08–7.69(m, 7H) |
| 214 | 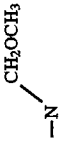 | CH$_3$ | H | H | O | O | O | O | Cl | H | H | Cl | 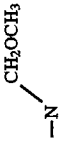 CH$_2$OCH$_3$ / CH$_3$ | 492(M$^+$) 323 295 | 1180 2210 | 50.97 3.70 11.30<br>51.13 3.68 11.36 | 1.08–1.73(m, 3H)<br>2.28(s, 3H)<br>3.52(s, 2H)<br>3.56(s, 3H)<br>4.35–5.25(m, 2H)<br>6.96–7.88(m, 7H) |
| 216 | 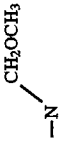 | H | C$_2$H$_5$ | H | O | O | O | O | H | H | H | H |  | 466(M$^+$) 257 243 | 1180 2220 | 59.11 4.60 12.00<br>59.22 4.75 12.01 | 1.13(t, 3H)<br>1.76(q, 2H)<br>2.22–2.38(m, 4H)<br>3.60–3.81(m, 4H)<br>4.73(s, 2H)<br>5.66(s, 1H)<br>7.08–7.96(m, 7H) |
| 218 |  H$_7$C$_3$O | CH$_3$ | H | H | O | O | O | O | H | H | H | H |  CH$_2$CO$_2$C$_2$H$_5$ / CN | 544(M$^+$) 322 294 | 1170 2210 | 63.88 5.05 10.38<br>63.96 5.18 10.29 | 0.89–1.88(m, 11H)<br>3.68–5.30(m, 8H)<br>7.02–8.00(m, 9H) |

TABLE 16

| Compound No. | A₁ | B₁ | B₂ | B₃ | X₁ | X₂ | X₃ | X₄ | Y₁ | Y₂ | Y₃ | Y₄ | —N(A₂)(A₃) | MASS | i.r.(cm⁻¹) (C—O—C, CN) | Elemental analysis C / H / N | ¹H-NMR |
|---|---|---|---|---|---|---|---|---|---|---|---|---|---|---|---|---|---|
| 220 | quinoxalin-2-yl | CH₃ | H | H | O | O | O | O | H | H | H | H | N-methyl-2,4-dichloroanilino | 534(M⁺) 265 237 | 1170 2220 | 60.63 3.88 10.35 / 60.57 3.77 10.47 | 1.00–1.82(m, 3H) 2.30(s, 3H) 4.40–5.30(m, 2H) 7.20–8.20(m, 11H) 8.81(s, 1H) |
| 222 | 6-bromoquinoxalin-2-yl | CH₃ | H | H | O | O | O | O | H | H | H | H | 3-nitroindol-1-yl | 599(M⁺) 343 315 | 1180 2210 | 55.89 3.00 11.46 / 56.01 3.02 11.67 | 1.10–1.80(m, 3H) 4.23–5.30(m, 2H) 6.88–8.24(m, 12H) 8.83(s, 1H) |
| 224 | 6-chloroquinoxalin-2-yl | H | H | H | O | O | O | O | H | H | H | H | piperidin-1-yl | 464(M⁺) 299 271 | 1190 2210 | 61.89 4.40 11.99 / 62.00 4.55 12.05 | 1.38–1.78(m, 6H) 2.24–2.48(m, 4H) 4.70(s, 2H) 5.57(s, 1H) 7.03–8.20(m, 7H) 8.80(s, 1H) |

TABLE 17

| Compound No. | A₁ | B₁ | B₂ | B₃ | X₁ | X₂ | X₃ | X₄ | Y₁ | Y₂ | Y₃ | Y₄ | $-N\stackrel{A_2}{\diagdown}_{A_3}$ | MASS | i.r.(cm⁻¹) (C—O—C,CN) | Elemental analysis C H N | ¹H-NMR |
|---|---|---|---|---|---|---|---|---|---|---|---|---|---|---|---|---|---|
| 238 | 3-Cl-5-CF₃-pyridin-2-yl | CH₃ | H | H | O | O | O | O | H | H | H | H | 3,5-dimethylpiperidin-1-yl | 523(M⁺) 316 288 | 1190 2210 | 57.33 4.66 7.94 57.31 4.77 8.02 | 0.90–2.62(m, 15H) 4.50(m, 2H) 5.30(q, 1H) 7.04(s, 4H) 7.98–8.26(m, 2H) |
| 245 | 3-Cl-5-CF₃-pyridin-2-yl | CH₃ | H | H | O | O | O | O | H | H | H | H | 1,2,3,4-tetrahydroquinolin-1-yl | 543(M⁺) 316 288 | 1190 2210 | 60.89 4.01 7.98 61.18 4.00 8.00 | 1.25–2.83(m, 7H) 3.80(m, 2H) 5.23(q, 1H) 6.99–7.32(m, 8H) 7.80–8.21(m, 2H) |
| 246 | 3-Cl-5-CF₃-pyridin-2-yl | CH₃ | H | H | O | O | O | O | H | H | H | H | N(nBu)₂ | 535(M⁺) 316 288 | 1180 2220 | 56.77 5.40 7.58 57.83 5.38 7.78 | 0.90–1.80(m, 17H) 3.30–3.70(m, 4H) 5.34(q, 1H) 7.05(bs, 4H) 7.97–8.26(m, 2H) |
| 248 | 3-Cl-5-CF₃-pyridin-2-yl | CH₃ | H | H | O | O | O | O | H | H | H | H | N(C₂H₅)(CH₂Ph) | 545(M⁺) 316 288 | 1180 2220 | 59.00 4.21 7.80 59.40 4.22 7.70 | 1.27(t, 3H) 1.70(d, 3H) 4.76(s, 2H) 5.35(q, 1H) 5.65(q, 1H) 7.05–7.31(m, 9H) 7.95–8.25(m, 2H) |

TABLE 18

| Compound No. | A₁ | B₁ | B₂ | B₃ | X₁ | X₂ | X₃ | X₄ | Y₁ | Y₂ | Y₃ | Y₄ | -N(A₂)(A₃) | MASS | i.r.(cm⁻¹) (C—O—C, CN) | Elemental analysis C | H | N | ¹H-NMR |
|---|---|---|---|---|---|---|---|---|---|---|---|---|---|---|---|---|---|---|---|
| 257 | 4-CF₃, 3-Cl phenyl | CH₃ | H | H | O | O | O | O | H | H | H | H | pyrrolidinyl | 480(M⁺) 315 287 | 1190 2210 | 57.33 57.44 | 4.10 4.16 | 5.78 5.83 | 1.64–1.96(m, 7H) 3.76(bs, 4H) 5.25(q, 1H) 6.81–7.71(m, 7H) |
| 260 | 4-CF₃, 3-Cl phenyl | CH₃ | H | H | O | O | O | O | H | H | H | H | N(CH₃)(Ph) | 516(M⁺) 315 287 | 1180 2220 | 59.93 60.41 | 3.77 3.87 | 5.39 5.42 | 1.60(d, 3H) 3.38(s, 3H) 5.15(q, 1H) 6.80–7.70(m, 12H) |
| 263 | 4-CF₃, 3-Cl phenyl | CH₃ | H | H | O | O | O | O | H | H | H | H | N(CH₂Ph)₂ | 606(M⁺) 315 287 | 1190 2220 | 65.30 65.29 | 4.30 4.29 | 4.60 4.62 | 1.68(d, 3H) 4.76(bs, 4H) 5.28(q, 1H) 6.70–7.68(m, 17H) |

Example 8 (Herbicide Preparation Example 1)

10 Parts by weight of the above cyanoketone derivative, 2 parts by weight of polyoxyethylene phenyl ether and 88 parts by weight of finely powdered clay were pulverized and mixed to give a 10% wettable powder.

Example 9 (Herbicide Preparation Example 2)

20 Parts by weight of the above cyanoketone derivative, 70 parts by weight of xylene and 10 parts by weight of a surfactant were mixed and dissolved to give a 20% emulsifiable concentrate.

Example 10 (Herbicide Preparation Example 3)

5 Parts by weight of the above cyanoketone derivative, 50 parts by weight of bentonire, 40 parts by weight of water and 5 parts by weight of Sorpol 800A(TOHO CHEMICAL INDUSTRY CO., LTD) as a surfactant were mixed and pulverized to form a paste. The paste was extruded through holes having a diameter of 0.7 mm, and the extrudate was dried and cut to a length of 1 to 2 mm to give 5% granules.

Example 11 (Herbicidal effect by foliar application)

Upland farm soil (clay loam) was filled in ⅛, 850-are pots, and seeds of barnyardgrass, green foxtail, blue morningglory, slender amaranth and hairy beggarticks were sown 0.5 to 1 cm deep. When these weeds grown to two- or three-leaf stage, a wetting agent was added to solutions prepared by diluting wettable powders of the compounds with water, and a predetermined amount of each of the mixtures was sprayed to the foliage. After the application, the weeds were allowed to grow in a greenhouse at an average temperature of 25° C. for 2 weeks, and then the herbicidal effects of compounds tested were examined. In addition to compounds of the present invention, the comparative compound (No.14) of the following formula

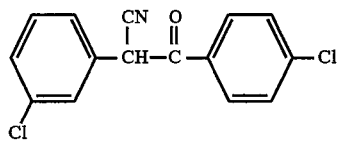

was also tested.

The results are shown in Tables 19 to 25.

In addition, the above herbicidal effects were evaluated on the basis of the following six ratings, 0 to 5.

0 ... control of weeds 0–9%
1 ... control of weeds 10–29%
2 ... control of weeds 30–49%
3 ... control of weeds 50–69%
4 ... control of weeds 70–89%
5 ... control of weeds 90–100%

TABLE 19

| Compound No. | Active component kg/ha | Barnyard-grass | Green foxtail | Blue morning glory | Slender amaranth | Hairy beggar-ticks |
|---|---|---|---|---|---|---|
| 100 | 3.0 | 5 | 5 | 0 | 1 | 0 |
|  | 2.0 | 5 | 5 | 0 | 0 | 0 |
|  | 1.0 | 5 | 5 | 0 | 0 | 0 |
| 102 | 3.0 | 5 | 5 | 0 | 0 | 0 |
|  | 2.0 | 5 | 5 | 0 | 0 | 0 |
|  | 1.0 | 4 | 4 | 0 | 0 | 0 |
| 104 | 3.0 | 5 | 5 | 0 | 1 | 0 |
|  | 2.0 | 5 | 5 | 0 | 0 | 0 |
|  | 1.0 | 4 | 4 | 0 | 0 | 0 |
| 106 | 3.0 | 5 | 5 | 0 | 0 | 0 |
|  | 2.0 | 5 | 5 | 0 | 0 | 0 |
|  | 1.0 | 5 | 4 | 0 | 0 | 0 |
| 108 | 3.0 | 5 | 5 | 0 | 1 | 0 |
|  | 2.0 | 5 | 5 | 0 | 0 | 0 |
|  | 1.0 | 4 | 5 | 0 | 0 | 0 |
| 110 | 3.0 | 5 | 5 | 1 | 1 | 0 |
|  | 2.0 | 5 | 5 | 0 | 0 | 0 |
|  | 1.0 | 5 | 5 | 0 | 0 | 0 |
| 112 | 3.0 | 5 | 5 | 0 | 0 | 0 |
|  | 2.0 | 5 | 5 | 0 | 0 | 0 |
|  | 1.0 | 5 | 4 | 0 | 0 | 0 |
| 114 | 3.0 | 5 | 5 | 1 | 1 | 0 |
|  | 2.0 | 5 | 5 | 0 | 0 | 0 |
|  | 1.0 | 4 | 5 | 0 | 0 | 0 |
| 116 | 3.0 | 5 | 5 | 0 | 0 | 0 |
|  | 2.0 | 5 | 5 | 0 | 0 | 0 |
|  | 1.0 | 5 | 5 | 0 | 0 | 0 |
| 118 | 3.0 | 5 | 5 | 0 | 0 | 0 |
|  | 2.0 | 5 | 5 | 0 | 0 | 0 |
|  | 1.0 | 5 | 5 | 0 | 0 | 0 |
| 120 | 3.0 | 5 | 5 | 0 | 0 | 0 |
|  | 2.0 | 5 | 5 | 0 | 0 | 0 |
|  | 1.0 | 5 | 4 | 0 | 0 | 0 |
| 122 | 3.0 | 5 | 5 | 5 | 0 | 0 |
|  | 2.0 | 5 | 5 | 5 | 0 | 0 |
|  | 1.0 | 5 | 5 | 5 | 0 | 0 |

TABLE 20

| Compound No. | Active component kg/ha | Barnyard-grass | Green foxtail | Blue morning glory | Slender amaranth | Hairy beggar-ticks |
|---|---|---|---|---|---|---|
| 124 | 3.0 | 5 | 5 | 0 | 1 | 0 |
|  | 2.0 | 5 | 5 | 0 | 0 | 0 |
|  | 1.0 | 4 | 4 | 0 | 0 | 0 |
| 126 | 3.0 | 5 | 5 | 0 | 0 | 0 |
|  | 2.0 | 5 | 5 | 0 | 0 | 0 |
|  | 1.0 | 4 | 5 | 0 | 0 | 0 |
| 128 | 3.0 | 5 | 5 | 1 | 1 | 0 |
|  | 2.0 | 5 | 5 | 0 | 0 | 0 |
|  | 1.0 | 4 | 5 | 0 | 0 | 0 |
| 130 | 3.0 | 5 | 5 | 0 | 0 | 0 |
|  | 2.0 | 5 | 5 | 0 | 0 | 0 |
|  | 1.0 | 5 | 5 | 0 | 0 | 0 |
| 132 | 3.0 | 5 | 5 | 0 | 0 | 0 |
|  | 2.0 | 5 | 5 | 0 | 0 | 0 |
|  | 1.0 | 5 | 4 | 0 | 0 | 0 |
| 134 | 3.0 | 5 | 5 | 0 | 0 | 0 |
|  | 2.0 | 5 | 5 | 0 | 0 | 0 |
|  | 1.0 | 4 | 5 | 0 | 0 | 0 |
| 136 | 3.0 | 5 | 5 | 0 | 1 | 0 |
|  | 2.0 | 5 | 5 | 0 | 0 | 0 |
|  | 1.0 | 5 | 5 | 0 | 0 | 0 |
| 138 | 3.0 | 5 | 5 | 0 | 1 | 0 |
|  | 2.0 | 5 | 5 | 0 | 0 | 0 |
|  | 1.0 | 5 | 5 | 0 | 0 | 0 |
| 140 | 3.0 | 5 | 5 | 1 | 0 | 0 |
|  | 2.0 | 5 | 5 | 0 | 0 | 0 |
|  | 1.0 | 5 | 5 | 0 | 0 | 0 |
| 142 | 3.0 | 5 | 5 | 0 | 0 | 0 |
|  | 2.0 | 5 | 5 | 0 | 0 | 0 |
|  | 1.0 | 5 | 4 | 0 | 0 | 0 |
| 144 | 3.0 | 5 | 5 | 1 | 1 | 0 |
|  | 2.0 | 5 | 5 | 0 | 0 | 0 |
|  | 1.0 | 5 | 4 | 0 | 0 | 0 |
| 146 | 3.0 | 5 | 5 | 0 | 1 | 0 |
|  | 2.0 | 5 | 5 | 0 | 0 | 0 |
|  | 1.0 | 5 | 5 | 0 | 0 | 0 |

TABLE 21

| Compound No. | Active component kg/ha | Barnyard-grass | Green foxtail | Blue morning glory | Slender amaranth | Hairy beggar-ticks |
|---|---|---|---|---|---|---|
| 148 | 3.0 | 5 | 5 | 0 | 0 | 0 |
|  | 2.0 | 5 | 5 | 0 | 0 | 0 |
|  | 1.0 | 4 | 5 | 0 | 0 | 0 |
| 150 | 3.0 | 5 | 5 | 1 | 2 | 0 |
|  | 2.0 | 5 | 5 | 0 | 1 | 0 |
|  | 1.0 | 4 | 5 | 0 | 0 | 0 |
| 152 | 3.0 | 5 | 5 | 0 | 1 | 0 |
|  | 2.0 | 5 | 5 | 0 | 0 | 0 |
|  | 1.0 | 5 | 5 | 0 | 0 | 0 |
| 154 | 3.0 | 5 | 5 | 0 | 1 | 0 |
|  | 2.0 | 5 | 5 | 0 | 0 | 0 |
|  | 1.0 | 5 | 5 | 0 | 0 | 0 |
| 156 | 3.0 | 5 | 5 | 0 | 0 | 0 |
|  | 2.0 | 5 | 5 | 0 | 0 | 0 |
|  | 1.0 | 5 | 4 | 0 | 0 | 0 |
| 158 | 3.0 | 5 | 5 | 0 | 1 | 0 |
|  | 2.0 | 5 | 5 | 0 | 0 | 0 |
|  | 1.0 | 5 | 4 | 0 | 0 | 0 |
| 160 | 3.0 | 5 | 5 | 0 | 1 | 0 |
|  | 2.0 | 5 | 5 | 0 | 0 | 0 |
|  | 1.0 | 4 | 4 | 0 | 0 | 0 |
| 162 | 3.0 | 5 | 5 | 0 | 1 | 0 |
|  | 2.0 | 5 | 5 | 0 | 0 | 0 |
|  | 1.0 | 5 | 5 | 0 | 0 | 0 |
| 164 | 3.0 | 5 | 5 | 0 | 0 | 0 |

TABLE 21-continued

| | Herbicidal effect by foliar application | | | | |
|---|---|---|---|---|---|
| Compound No. | Active component kg/ha | Barnyard-grass | Green foxtail | Blue morning glory | Slender amaranth | Hairy beggar-ticks |
| | 2.0 | 5 | 5 | 0 | 0 | 0 |
| | 1.0 | 5 | 4 | 0 | 0 | 0 |
| 166 | 3.0 | 5 | 5 | 0 | 0 | 0 |
| | 2.0 | 5 | 5 | 0 | 0 | 0 |
| | 1.0 | 5 | 4 | 0 | 0 | 0 |
| 168 | 3.0 | 5 | 5 | 0 | 1 | 0 |
| | 2.0 | 5 | 5 | 0 | 0 | 0 |
| | 1.0 | 5 | 5 | 0 | 0 | 0 |
| 170 | 3.0 | 5 | 5 | 0 | 0 | 0 |
| | 2.0 | 5 | 5 | 0 | 0 | 0 |
| | 1.0 | 5 | 4 | 0 | 0 | 0 |

TABLE 22

| | Herbicidal effect by foliar application | | | | |
|---|---|---|---|---|---|
| Compound No. | Active component kg/ha | Barnyard-grass | Green foxtail | Blue morning glory | Slender amaranth | Hairy beggar-ticks |
| 172 | 3.0 | 5 | 5 | 0 | 0 | 0 |
| | 2.0 | 5 | 5 | 0 | 0 | 0 |
| | 1.0 | 5 | 5 | 0 | 0 | 0 |
| 174 | 3.0 | 5 | 5 | 0 | 0 | 0 |
| | 2.0 | 5 | 5 | 0 | 0 | 0 |
| | 1.0 | 4 | 4 | 0 | 0 | 0 |
| 176 | 3.0 | 5 | 5 | 0 | 0 | 0 |
| | 2.0 | 5 | 5 | 0 | 0 | 0 |
| | 1.0 | 4 | 5 | 0 | 0 | 0 |
| 178 | 3.0 | 5 | 5 | 0 | 0 | 0 |
| | 2.0 | 5 | 5 | 0 | 0 | 0 |
| | 1.0 | 4 | 5 | 0 | 0 | 0 |
| 180 | 3.0 | 5 | 5 | 0 | 0 | 0 |
| | 2.0 | 5 | 5 | 0 | 0 | 0 |
| | 1.0 | 5 | 5 | 0 | 0 | 0 |
| 182 | 3.0 | 5 | 5 | 0 | 0 | 0 |
| | 2.0 | 5 | 5 | 0 | 0 | 0 |
| | 1.0 | 4 | 5 | 0 | 0 | 0 |
| 184 | 3.0 | 5 | 5 | 0 | 1 | 0 |
| | 2.0 | 5 | 5 | 0 | 0 | 0 |
| | 1.0 | 5 | 5 | 0 | 0 | 0 |
| 186 | 3.0 | 5 | 5 | 0 | 0 | 0 |
| | 2.0 | 5 | 5 | 0 | 0 | 0 |
| | 1.0 | 4 | 4 | 0 | 0 | 0 |
| 188 | 3.0 | 5 | 5 | 0 | 0 | 0 |
| | 2.0 | 5 | 5 | 0 | 0 | 0 |
| | 1.0 | 4 | 4 | 0 | 0 | 0 |
| 190 | 3.0 | 5 | 5 | 0 | 1 | 0 |
| | 2.0 | 5 | 5 | 0 | 1 | 0 |
| | 1.0 | 5 | 5 | 0 | 0 | 0 |
| 192 | 3.0 | 5 | 5 | 0 | 1 | 0 |
| | 2.0 | 5 | 5 | 0 | 0 | 0 |
| | 1.0 | 5 | 4 | 0 | 0 | 0 |
| 194 | 3.0 | 5 | 5 | 0 | 0 | 0 |
| | 2.0 | 5 | 5 | 0 | 0 | 0 |
| | 1.0 | 5 | 4 | 0 | 0 | 0 |

TABLE 23

| | | Herbicidal effect by foliar application | | | | |
|---|---|---|---|---|---|---|
| Compound No. | Active component kg/ha | Barnyard-grass | Green foxtail | Blue morning glory | Slender amaranth | Hairy beggar-ticks |
| 196 | 3.0 | 5 | 5 | 0 | 1 | 0 |
| | 2.0 | 5 | 5 | 0 | 0 | 0 |
| | 1.0 | 4 | 5 | 0 | 0 | 0 |
| 198 | 3.0 | 5 | 5 | 1 | 1 | 1 |
| | 2.0 | 5 | 5 | 0 | 0 | 0 |
| | 1.0 | 4 | 5 | 0 | 0 | 0 |
| 200 | 3.0 | 5 | 5 | 1 | 1 | 0 |
| | 2.0 | 5 | 5 | 0 | 0 | 0 |
| | 1.0 | 5 | 4 | 0 | 0 | 0 |
| 202 | 3.0 | 5 | 5 | 0 | 0 | 0 |
| | 2.0 | 5 | 5 | 0 | 0 | 0 |
| | 1.0 | 5 | 4 | 0 | 0 | 0 |
| 204 | 3.0 | 5 | 5 | 0 | 0 | 0 |
| | 2.0 | 5 | 5 | 0 | 0 | 0 |
| | 1.0 | 4 | 4 | 0 | 0 | 0 |
| 206 | 3.0 | 5 | 5 | 0 | 1 | 0 |
| | 2.0 | 5 | 5 | 0 | 0 | 0 |
| | 1.0 | 5 | 5 | 0 | 0 | 0 |
| 208 | 3.0 | 5 | 5 | 1 | 1 | 0 |
| | 2.0 | 5 | 5 | 0 | 1 | 0 |
| | 1.0 | 5 | 5 | 0 | 0 | 0 |
| 210 | 3.0 | 5 | 5 | 0 | 0 | 0 |
| | 2.0 | 5 | 5 | 0 | 0 | 0 |
| | 1.0 | 5 | 5 | 0 | 0 | 0 |
| 212 | 3.0 | 5 | 5 | 0 | 0 | 0 |
| | 2.0 | 5 | 5 | 0 | 0 | 0 |
| | 1.0 | 4 | 5 | 0 | 0 | 0 |
| 214 | 3.0 | 5 | 5 | 0 | 0 | 0 |
| | 2.0 | 5 | 5 | 0 | 0 | 0 |
| | 1.0 | 4 | 5 | 0 | 0 | 0 |
| 216 | 3.0 | 5 | 5 | 0 | 0 | 0 |
| | 2.0 | 5 | 5 | 0 | 0 | 0 |
| | 1.0 | 5 | 4 | 0 | 0 | 0 |
| 218 | 3.0 | 5 | 5 | 0 | 1 | 0 |
| | 2.0 | 5 | 5 | 0 | 0 | 0 |
| | 1.0 | 4 | 4 | 0 | 0 | 0 |

TABLE 24

| | | Herbicidal effect by foliar application | | | | |
|---|---|---|---|---|---|---|
| Compound No. | Active component kg/ha | Barnyard-grass | Green foxtail | Blue morning glory | Slender amaranth | Hairy beggar-ticks |
| 220 | 3.0 | 5 | 5 | 0 | 0 | 0 |
| | 2.0 | 5 | 5 | 0 | 0 | 0 |
| | 1.0 | 5 | 4 | 0 | 0 | 0 |
| 222 | 3.0 | 5 | 5 | 0 | 0 | 0 |
| | 2.0 | 5 | 5 | 0 | 0 | 0 |
| | 1.0 | 4 | 5 | 0 | 0 | 0 |
| 224 | 3.0 | 5 | 5 | 0 | 0 | 0 |
| | 2.0 | 5 | 5 | 0 | 0 | 0 |
| | 1.0 | 4 | 5 | 0 | 0 | 0 |
| 150 (a) | 3.0 | 5 | 5 | 0 | 0 | 0 |
| | 2.0 | 5 | 5 | 0 | 0 | 0 |
| | 1.0 | 4 | 5 | 0 | 0 | 0 |
| 238 | 3.0 | 5 | 5 | 0 | 0 | 0 |
| | 2.0 | 5 | 5 | 0 | 0 | 0 |
| | 1.0 | 5 | 5 | 0 | 0 | 0 |
| 245 | 3.0 | 5 | 5 | 0 | 0 | 0 |
| | 2.0 | 5 | 5 | 0 | 0 | 0 |
| | 1.0 | 5 | 5 | 0 | 0 | 0 |
| 246 | 3.0 | 5 | 5 | 0 | 0 | 0 |
| | 2.0 | 5 | 5 | 0 | 0 | 0 |
| | 1.0 | 5 | 4 | 0 | 0 | 0 |

TABLE 25

| Compound No. | Active component kg/ha | Barnyard-grass | Green foxtail | Blue morning glory | Slender amaranth | Hairy beggar-ticks |
|---|---|---|---|---|---|---|
| 248 | 3.0 | 5 | 5 | 0 | 0 | 0 |
|  | 2.0 | 5 | 5 | 0 | 0 | 0 |
|  | 1.0 | 5 | 4 | 0 | 0 | 0 |
| 257 | 3.0 | 5 | 5 | 0 | 0 | 0 |
|  | 2.0 | 5 | 5 | 0 | 0 | 0 |
|  | 1.0 | 4 | 4 | 0 | 0 | 0 |
| 260 | 3.0 | 5 | 5 | 0 | 0 | 0 |
|  | 2.0 | 5 | 5 | 0 | 0 | 0 |
|  | 1.0 | 4 | 4 | 0 | 0 | 0 |
| 263 | 3.0 | 5 | 5 | 0 | 0 | 0 |
|  | 2.0 | 5 | 5 | 0 | 0 | 0 |
|  | 1.0 | 4 | 4 | 0 | 0 | 0 |
| 14 | 3.0 | 3 | 4 | 3 | 3 | 2 |
|  | 2.0 | 2 | 2 | 2 | 2 | 1 |
|  | 1.0 | 1 | 1 | 1 | 1 | 0 |
| 1100* | 3.0 | 5 | 5 | 0 | 0 | 0 |
|  | 2.0 | 5 | 5 | 0 | 0 | 0 |
|  | 1.0 | 3 | 2 | 0 | 0 | 0 |
| 1240** | 3.0 | 5 | 5 | 0 | 0 | 0 |
|  | 2.0 | 5 | 5 | 0 | 0 | 0 |
|  | 1.0 | 2 | 3 | 0 | 0 | 0 |

(Note)
*1100 (Comparative Example): 1-cyano-1-(3-methoxy-phenyl)-3-[4-(4-fluorophenoxy)phenoxy]acetone
**1240 (Comparative Example): 1-cyano-1-(2,4-dichloro-phenyl)-3-[4-(3-chloro-5-trifluoromethyl-2-pyridyloxy)phenoxy]-acetone Example 12 (Test on phytotoxicity on crops by foliar application)

Upland farm soil (clay loam) was filled in ⅛ 850-are pots, and seeds of soybean, adzuki bean and beet were sown 1.5 to 2 cm deep. When the soybean grown to a primary leaf development stage, the predetermined amount of each of the solutions prepared by diluting each of wettable powders of the compounds with water was sprayed to the foliage. After this application, these crops were allowed to grow in a greenhouse at an average temperature of 25° C. for 2 weeks, and then the phytotoxicity of each of the test compounds on the crops was examined. The results are shown in Tables 26 to 30.

The herbicide injury was evaluated as follows. The ratios of the height and total weight (air-dried weight) of an applied lot to those of an unapplied lot were calculated. The lowest ratios of these factors were taken as 5, and the phytotoxicity was evaluated on the basis of the following six ratings 0 to 5.

0 ... ratio to unapplied lot 100%
1 ... ratio to unapplied lot 90–99%
2 ... ratio to unapplied lot 80–89%
3 ... ratio to unapplied lot 60–79%
4 ... ratio to unapplied lot 40–59%
5 ... ratio to unapplied lot 0–39%

TABLE 26

| Compound No. | Active component kg/ha | Soybeans | Adzuki-beans | BEET |
|---|---|---|---|---|
| 100 | 3.0 | 0 | 0 | 0 |
|  | 2.0 | 0 | 0 | 0 |
| 102 | 3.0 | 0 | 0 | 0 |
|  | 2.0 | 0 | 0 | 0 |
| 104 | 3.0 | 0 | 0 | 1 |
|  | 2.0 | 0 | 0 | 0 |
| 106 | 3.0 | 0 | 0 | 1 |
|  | 2.0 | 0 | 0 | 0 |
| 108 | 3.0 | 0 | 0 | 1 |
|  | 2.0 | 0 | 0 | 0 |
| 110 | 3.0 | 0 | 0 | 1 |
|  | 2.0 | 0 | 0 | 0 |
| 112 | 3.0 | 0 | 0 | 0 |
|  | 2.0 | 0 | 0 | 0 |
| 114 | 3.0 | 1 | 0 | 1 |
|  | 2.0 | 0 | 0 | 0 |
| 116 | 3.0 | 0 | 0 | 1 |
|  | 2.0 | 0 | 0 | 0 |
| 118 | 3.0 | 0 | 0 | 1 |
|  | 2.0 | 0 | 0 | 0 |
| 120 | 3.0 | 1 | 0 | 1 |
|  | 2.0 | 0 | 0 | 0 |
| 122 | 3.0 | 0 | 0 | 1 |
|  | 2.0 | 0 | 0 | 0 |
| 124 | 3.0 | 0 | 0 | 0 |
|  | 2.0 | 0 | 0 | 0 |
| 126 | 3.0 | 0 | 0 | 1 |
|  | 2.0 | 0 | 0 | 0 |
| 128 | 3.0 | 0 | 0 | 1 |
|  | 2.0 | 0 | 0 | 0 |
| 130 | 3.0 | 0 | 0 | 0 |
|  | 2.0 | 0 | 0 | 0 |

TABLE 27

| Compound No. | Active component kg/ha | Phytotoxicity by foliar application | | |
|---|---|---|---|---|
| | | Soybeans | Adzuki-beans | BEET |
| 132 | 3.0 | 0 | 0 | 0 |
| | 2.0 | 0 | 0 | 0 |
| 134 | 3.0 | 0 | 0 | 0 |
| | 2.0 | 0 | 0 | 0 |
| 136 | 3.0 | 1 | 1 | 1 |
| | 2.0 | 0 | 0 | 0 |
| 138 | 3.0 | 1 | 0 | 1 |
| | 2.0 | 0 | 0 | 0 |
| 140 | 3.0 | 0 | 0 | 1 |
| | 2.0 | 0 | 0 | 0 |
| 142 | 3.0 | 0 | 0 | 0 |
| | 2.0 | 0 | 0 | 0 |
| 144 | 3.0 | 0 | 0 | 1 |
| | 2.0 | 0 | 0 | 1 |
| 146 | 3.0 | 0 | 0 | 1 |
| | 2.0 | 0 | 0 | 0 |
| 148 | 3.0 | 0 | 0 | 0 |
| | 2.0 | 0 | 0 | 0 |
| 150 | 3.0 | 0 | 0 | 0 |
| | 2.0 | 0 | 0 | 0 |
| 152 | 3.0 | 0 | 0 | 1 |
| | 2.0 | 0 | 0 | 0 |
| 154 | 3.0 | 0 | 0 | 1 |
| | 2.0 | 0 | 0 | 0 |
| 156 | 3.0 | 0 | 0 | 0 |
| | 2.0 | 0 | 0 | 0 |
| 158 | 3.0 | 0 | 0 | 0 |
| | 2.0 | 0 | 0 | 0 |
| 160 | 3.0 | 0 | 0 | 1 |
| | 2.0 | 0 | 0 | 0 |
| 162 | 3.0 | 1 | 0 | 1 |
| | 2.0 | 0 | 0 | 0 |

TABLE 28

| Compound No. | Active component kg/ha | Phytotoxicity by foliar application | | |
|---|---|---|---|---|
| | | Soybeans | Adzuki-beans | BEET |
| 164 | 3.0 | 0 | 0 | 0 |
| | 2.0 | 0 | 0 | 0 |
| 166 | 3.0 | 0 | 0 | 0 |
| | 2.0 | 0 | 0 | 0 |
| 168 | 3.0 | 0 | 0 | 0 |
| | 2.0 | 0 | 0 | 0 |
| 170 | 3.0 | 0 | 0 | 1 |
| | 2.0 | 0 | 0 | 0 |
| 172 | 3.0 | 0 | 0 | 1 |
| | 2.0 | 0 | 0 | 0 |
| 174 | 3.0 | 1 | 1 | 1 |
| | 2.0 | 0 | 0 | 0 |
| 176 | 3.0 | 0 | 0 | 0 |
| | 2.0 | 0 | 0 | 0 |
| 178 | 3.0 | 1 | 0 | 1 |
| | 2.0 | 0 | 0 | 0 |
| 180 | 3.0 | 0 | 0 | 0 |
| | 2.0 | 0 | 0 | 0 |
| 182 | 3.0 | 0 | 0 | 1 |
| | 2.0 | 0 | 0 | 0 |
| 184 | 3.0 | 0 | 0 | 1 |
| | 2.0 | 0 | 0 | 0 |
| 186 | 3.0 | 0 | 0 | 0 |
| | 2.0 | 0 | 0 | 0 |
| 188 | 3.0 | 0 | 0 | 1 |
| | 2.0 | 0 | 0 | 0 |
| 190 | 3.0 | 1 | 1 | 1 |
| | 2.0 | 0 | 0 | 0 |
| 192 | 3.0 | 0 | 0 | 1 |
| | 2.0 | 0 | 0 | 0 |
| 194 | 3.0 | 0 | 0 | 1 |
| | 2.0 | 0 | 0 | 0 |

TABLE 29

| Compound No. | Active component kg/ha | Phytotoxicity by foliar application | | |
|---|---|---|---|---|
| | | Soybeans | Adzuki-beans | BEET |
| 196 | 3.0 | 1 | 1 | 1 |
| | 2.0 | 0 | 0 | 0 |
| 198 | 3.0 | 1 | 0 | 1 |
| | 2.0 | 0 | 0 | 0 |
| 200 | 3.0 | 1 | 0 | 1 |
| | 2.0 | 0 | 0 | 0 |
| 202 | 3.0 | 0 | 0 | 0 |
| | 2.0 | 0 | 0 | 0 |
| 204 | 3.0 | 0 | 0 | 1 |
| | 2.0 | 0 | 0 | 0 |
| 206 | 3.0 | 1 | 0 | 1 |
| | 2.0 | 1 | 0 | 0 |
| 208 | 3.0 | 1 | 0 | 1 |
| | 2.0 | 0 | 0 | 0 |
| 210 | 3.0 | 0 | 0 | 0 |
| | 2.0 | 0 | 0 | 0 |
| 212 | 3.0 | 0 | 0 | 0 |
| | 2.0 | 0 | 0 | 0 |
| 214 | 3.0 | 0 | 0 | 0 |
| | 2.0 | 0 | 0 | 0 |
| 216 | 3.0 | 0 | 0 | 0 |
| | 2.0 | 0 | 0 | 0 |
| 218 | 3.0 | 0 | 0 | 1 |
| | 2.0 | 0 | 0 | 0 |
| 220 | 3.0 | 0 | 0 | 0 |
| | 2.0 | 0 | 0 | 0 |
| 222 | 3.0 | 0 | 0 | 1 |
| | 2.0 | 0 | 0 | 0 |
| 224 | 3.0 | 0 | 0 | 1 |
| | 2.0 | 0 | 0 | 0 |
| 150 (a) | 3.0 | 0 | 0 | 0 |
| | 2.0 | 0 | 0 | 0 |

TABLE 30

| Compound No. | Active component kg/ha | Phytotoxicity by foliar application | | |
|---|---|---|---|---|
| | | Soybeans | Adzuki-beans | BEET |
| 238 | 3.0 | 0 | 1 | 0 |
| | 2.0 | 0 | 0 | 0 |
| 245 | 3.0 | 0 | 0 | 1 |
| | 2.0 | 0 | 0 | 0 |
| 246 | 3.0 | 1 | 0 | 1 |
| | 2.0 | 0 | 0 | 0 |
| 248 | 3.0 | 0 | 0 | 1 |
| | 2.0 | 0 | 0 | 0 |
| 257 | 3.0 | 0 | 0 | 0 |
| | 2.0 | 0 | 0 | 0 |
| 260 | 3.0 | 1 | 0 | 0 |
| | 2.0 | 0 | 0 | 0 |
| 263 | 3.0 | 0 | 0 | 0 |
| | 2.0 | 0 | 0 | 0 |

Example 12 (Test on herbicidal effect by upland farm soil application)

Upland farm soil (clay loom) was filled in 1/8, 850-are pots, and seeds of barnyardgrass, green foxtail, slender amaranth and hairy beggarticks were sown 0.5 to 1 cm deep. Then, the predetermined amount of each of the solutions prepared by diluting the wettable powders of the compounds with water was sprayed to the soil. After the application, the weeds were allowed to grow in a greenhouse at an average temperature of 25° C. for 2 weeks, and then the herbicidal effects of the test compounds were examined in the same manner as the above Table. The results are shown in Tables 31 to 36.

TABLE 31

| | Herbicidal effect by upland soil application | | | |
|---|---|---|---|---|
| Compound No. | Active component kg/ha | Barn-yard-grass | Green foxtail | Slender amaranth | Hairy beggar-ticks |
| 100 | 3.0 | 5 | 5 | 0 | 0 |
| | 2.0 | 5 | 5 | 0 | 0 |
| | 1.0 | 5 | 5 | 0 | 0 |
| 102 | 3.0 | 5 | 5 | 0 | 0 |
| | 2.0 | 5 | 5 | 0 | 0 |
| | 1.0 | 5 | 4 | 0 | 0 |
| 104 | 3.0 | 5 | 5 | 0 | 0 |
| | 2.0 | 5 | 5 | 0 | 0 |
| | 1.0 | 5 | 4 | 0 | 0 |
| 106 | 3.0 | 5 | 5 | 0 | 0 |
| | 2.0 | 5 | 5 | 0 | 0 |
| | 1.0 | 4 | 4 | 0 | 0 |
| 108 | 3.0 | 5 | 5 | 0 | 0 |
| | 2.0 | 5 | 5 | 0 | 0 |
| | 1.0 | 5 | 4 | 0 | 0 |
| 110 | 3.0 | 5 | 5 | 1 | 0 |
| | 2.0 | 5 | 5 | 0 | 0 |
| | 1.0 | 5 | 4 | 0 | 0 |
| 112 | 3.0 | 5 | 5 | 0 | 0 |
| | 2.0 | 5 | 5 | 0 | 0 |
| | 1.0 | 4 | 5 | 0 | 0 |
| 114 | 3.0 | 5 | 5 | 1 | 0 |
| | 2.0 | 5 | 5 | 0 | 0 |
| | 1.0 | 4 | 5 | 0 | 0 |
| 116 | 3.0 | 5 | 5 | 0 | 0 |
| | 2.0 | 5 | 5 | 0 | 0 |
| | 1.0 | 5 | 5 | 0 | 0 |
| 118 | 3.0 | 5 | 5 | 0 | 0 |
| | 2.0 | 5 | 5 | 0 | 0 |
| | 1.0 | 5 | 5 | 0 | 0 |
| 120 | 3.0 | 5 | 5 | 0 | 0 |
| | 2.0 | 5 | 5 | 0 | 0 |
| | 1.0 | 4 | 5 | 0 | 0 |
| 122 | 3.0 | 5 | 5 | 0 | 0 |
| | 2.0 | 5 | 5 | 0 | 0 |
| | 1.0 | 5 | 5 | 0 | 0 |

TABLE 32

| | Herbicidal effect by upland soil application | | | |
|---|---|---|---|---|
| Compound No. | Active component kg/ha | Barn-yard-grass | Green foxtail | Slender amaranth | Hairy beggar-ticks |
| 124 | 3.0 | 5 | 5 | 0 | 0 |
| | 2.0 | 5 | 5 | 0 | 0 |
| | 1.0 | 5 | 5 | 0 | 0 |
| 126 | 3.0 | 5 | 5 | 1 | 0 |
| | 2.0 | 5 | 5 | 0 | 0 |
| | 1.0 | 5 | 5 | 0 | 0 |
| 128 | 3.0 | 5 | 5 | 1 | 0 |
| | 2.0 | 5 | 5 | 0 | 0 |
| | 1.0 | 5 | 4 | 0 | 0 |

TABLE 32-continued

| | Herbicidal effect by upland soil application | | | |
|---|---|---|---|---|
| Compound No. | Active component kg/ha | Barn-yard-grass | Green foxtail | Slender amaranth | Hairy beggar-ticks |
| 130 | 3.0 | 5 | 5 | 0 | 0 |
| | 2.0 | 5 | 5 | 0 | 0 |
| | 1.0 | 5 | 5 | 0 | 0 |
| 132 | 3.0 | 5 | 5 | 0 | 0 |
| | 2.0 | 5 | 5 | 0 | 0 |
| | 1.0 | 4 | 5 | 0 | 0 |
| 134 | 3.0 | 5 | 5 | 0 | 0 |
| | 2.0 | 5 | 5 | 0 | 0 |
| | 1.0 | 4 | 5 | 0 | 0 |
| 136 | 3.0 | 5 | 5 | 1 | 0 |
| | 2.0 | 5 | 5 | 0 | 0 |
| | 1.0 | 5 | 5 | 0 | 0 |
| 138 | 3.0 | 5 | 5 | 1 | 0 |
| | 2.0 | 5 | 5 | 0 | 0 |
| | 1.0 | 4 | 5 | 0 | 0 |
| 140 | 3.0 | 5 | 5 | 1 | 0 |
| | 2.0 | 5 | 5 | 0 | 0 |
| | 1.0 | 4 | 5 | 0 | 0 |
| 142 | 3.0 | 5 | 5 | 0 | 0 |
| | 2.0 | 5 | 5 | 0 | 0 |
| | 1.0 | 4 | 4 | 0 | 0 |
| 144 | 3.0 | 5 | 5 | 1 | 0 |
| | 2.0 | 5 | 5 | 1 | 0 |
| | 1.0 | 5 | 5 | 0 | 0 |
| 146 | 3.0 | 5 | 5 | 1 | 0 |
| | 2.0 | 5 | 5 | 0 | 0 |
| | 1.0 | 5 | 4 | 0 | 0 |

TABLE 33

| | Herbicidal effect by upland soil application | | | |
|---|---|---|---|---|
| Compound No. | Active component kg/ha | Barn-yard-grass | Green foxtail | Slender amaranth | Hairy beggar-ticks |
| 148 | 3.0 | 5 | 5 | 0 | 0 |
| | 2.0 | 5 | 5 | 0 | 0 |
| | 1.0 | 5 | 5 | 0 | 0 |
| 150 | 3.0 | 5 | 5 | 1 | 0 |
| | 2.0 | 5 | 5 | 1 | 0 |
| | 1.0 | 5 | 5 | 0 | 0 |
| 152 | 3.0 | 5 | 5 | 0 | 0 |
| | 2.0 | 5 | 5 | 0 | 0 |
| | 1.0 | 5 | 5 | 0 | 0 |
| 154 | 3.0 | 5 | 5 | 0 | 0 |
| | 2.0 | 5 | 5 | 0 | 0 |
| | 1.0 | 5 | 5 | 0 | 0 |
| 156 | 3.0 | 5 | 5 | 0 | 0 |
| | 2.0 | 5 | 5 | 0 | 0 |
| | 1.0 | 5 | 4 | 0 | 0 |
| 158 | 3.0 | 5 | 5 | 1 | 0 |
| | 2.0 | 5 | 5 | 0 | 0 |
| | 1.0 | 5 | 4 | 0 | 0 |
| 160 | 3.0 | 5 | 5 | 1 | 0 |
| | 2.0 | 5 | 5 | 0 | 0 |
| | 1.0 | 5 | 5 | 0 | 0 |
| 162 | 3.0 | 5 | 5 | 1 | 0 |
| | 2.0 | 5 | 5 | 0 | 0 |
| | 1.0 | 4 | 5 | 0 | 0 |
| 164 | 3.0 | 5 | 5 | 0 | 0 |
| | 2.0 | 5 | 5 | 0 | 0 |
| | 1.0 | 4 | 5 | 0 | 0 |
| 166 | 3.0 | 5 | 5 | 0 | 0 |
| | 2.0 | 5 | 5 | 0 | 0 |
| | 1.0 | 4 | 5 | 0 | 0 |
| 168 | 3.0 | 5 | 5 | 0 | 0 |
| | 2.0 | 5 | 5 | 0 | 0 |
| | 1.0 | 5 | 4 | 0 | 0 |
| 170 | 3.0 | 5 | 5 | 0 | 0 |

TABLE 33-continued

Herbicidal effect by upland soil application

| Compound No. | Active component kg/ha | Barn-yard-grass | Green foxtail | Slender amaranth | Hairy beggar-ticks |
|---|---|---|---|---|---|
| | 2.0 | 5 | 5 | 0 | 0 |
| | 1.0 | 5 | 5 | 0 | 0 |

TABLE 34

Herbicidal effect by upland soil application

| Compound No. | Active component kg/ha | Barn-yard-grass | Green foxtail | Slender amaranth | Hairy beggar-ticks |
|---|---|---|---|---|---|
| 172 | 3.0 | 5 | 5 | 1 | 0 |
| | 2.0 | 5 | 5 | 0 | 0 |
| | 1.0 | 5 | 5 | 0 | 0 |
| 174 | 3.0 | 5 | 5 | 0 | 0 |
| | 2.0 | 5 | 5 | 0 | 0 |
| | 1.0 | 4 | 4 | 0 | 0 |
| 176 | 3.0 | 5 | 5 | 0 | 0 |
| | 2.0 | 5 | 5 | 0 | 0 |
| | 1.0 | 5 | 4 | 0 | 0 |
| 178 | 3.0 | 5 | 5 | 1 | 0 |
| | 2.0 | 5 | 5 | 0 | 0 |
| | 1.0 | 5 | 5 | 0 | 0 |
| 180 | 3.0 | 5 | 5 | 0 | 0 |
| | 2.0 | 5 | 5 | 0 | 0 |
| | 1.0 | 5 | 5 | 0 | 0 |
| 182 | 3.0 | 5 | 5 | 0 | 0 |
| | 2.0 | 5 | 5 | 0 | 0 |
| | 1.0 | 5 | 5 | 0 | 0 |
| 184 | 3.0 | 5 | 5 | 0 | 0 |
| | 2.0 | 5 | 5 | 0 | 0 |
| | 1.0 | 5 | 5 | 0 | 0 |
| 186 | 3.0 | 5 | 5 | 0 | 0 |
| | 2.0 | 5 | 5 | 0 | 0 |
| | 1.0 | 4 | 5 | 0 | 0 |
| 188 | 3.0 | 5 | 5 | 0 | 0 |
| | 2.0 | 5 | 5 | 0 | 0 |
| | 1.0 | 5 | 4 | 0 | 0 |
| 190 | 3.0 | 5 | 5 | 1 | 0 |
| | 2.0 | 5 | 5 | 1 | 0 |
| | 1.0 | 4 | 5 | 0 | 0 |
| 192 | 3.0 | 5 | 5 | 1 | 0 |
| | 2.0 | 5 | 5 | 0 | 0 |
| | 1.0 | 5 | 4 | 0 | 0 |
| 194 | 3.0 | 5 | 5 | 1 | 0 |
| | 2.0 | 5 | 5 | 0 | 0 |
| | 1.0 | 4 | 5 | 0 | 0 |

TABLE 35

Herbicidal effect by upland soil application

| Compound No. | Active component kg/ha | Barn-yard-grass | Green foxtail | Slender amaranth | Hairy beggar-ticks |
|---|---|---|---|---|---|
| 196 | 3.0 | 5 | 5 | 0 | 0 |
| | 2.0 | 5 | 5 | 0 | 0 |
| | 1.0 | 5 | 4 | 0 | 0 |
| 198 | 3.0 | 5 | 5 | 1 | 0 |
| | 2.0 | 5 | 5 | 0 | 0 |
| | 1.0 | 5 | 4 | 0 | 0 |
| 200 | 3.0 | 5 | 5 | 1 | 0 |
| | 2.0 | 5 | 5 | 0 | 0 |
| | 1.0 | 5 | 4 | 0 | 0 |
| 202 | 3.0 | 5 | 5 | 0 | 0 |
| | 2.0 | 5 | 5 | 0 | 0 |
| | 1.0 | 5 | 4 | 0 | 0 |
| 204 | 3.0 | 5 | 5 | 0 | 0 |
| | 2.0 | 5 | 5 | 0 | 0 |
| | 1.0 | 4 | 5 | 0 | 0 |
| 206 | 3.0 | 5 | 5 | 1 | 0 |
| | 2.0 | 5 | 5 | 0 | 0 |
| | 1.0 | 5 | 5 | 0 | 0 |
| 208 | 3.0 | 5 | 5 | 1 | 0 |
| | 2.0 | 5 | 5 | 0 | 0 |
| | 1.0 | 5 | 5 | 0 | 0 |
| 210 | 3.0 | 5 | 5 | 0 | 0 |
| | 2.0 | 5 | 5 | 0 | 0 |
| | 1.0 | 5 | 5 | 0 | 0 |
| 212 | 3.0 | 5 | 5 | 0 | 0 |
| | 2.0 | 5 | 5 | 0 | 0 |
| | 1.0 | 5 | 4 | 0 | 0 |
| 214 | 3.0 | 5 | 5 | 0 | 0 |
| | 2.0 | 5 | 5 | 0 | 0 |
| | 1.0 | 4 | 4 | 0 | 0 |
| 216 | 3.0 | 5 | 5 | 0 | 0 |
| | 2.0 | 5 | 5 | 0 | 0 |
| | 1.0 | 5 | 4 | 0 | 0 |
| 218 | 3.0 | 5 | 5 | 1 | 0 |
| | 2.0 | 5 | 5 | 0 | 0 |
| | 1.0 | 5 | 5 | 0 | 0 |

TABLE 36

Herbicidal effect by upland soil application

| Compound No. | Active component kg/ha | Barn-yard-grass | Green foxtail | Slender amaranth | Hairy beggar-ticks |
|---|---|---|---|---|---|
| 220 | 3.0 | 5 | 5 | 0 | 0 |
| | 2.0 | 5 | 5 | 0 | 0 |
| | 1.0 | 4 | 5 | 0 | 0 |
| 222 | 3.0 | 5 | 5 | 1 | 0 |
| | 2.0 | 5 | 5 | 0 | 0 |
| | 1.0 | 4 | 5 | 0 | 0 |
| 224 | 3.0 | 5 | 5 | 0 | 0 |
| | 2.0 | 5 | 5 | 0 | 0 |
| | 1.0 | 5 | 4 | 0 | 0 |
| 150 (a) | 3.0 | 5 | 5 | 1 | 0 |
| | 2.0 | 5 | 5 | 0 | 0 |
| | 1.0 | 5 | 5 | 0 | 0 |
| 150 (b) | 3.0 | 5 | 5 | 1 | 0 |
| | 2.0 | 5 | 5 | 0 | 0 |
| | 1.0 | 5 | 5 | 0 | 0 |
| 238 | 3.0 | 5 | 5 | 0 | 0 |
| | 2.0 | 5 | 5 | 0 | 0 |
| | 1.0 | 5 | 4 | 0 | 0 |
| 245 | 3.0 | 5 | 5 | 1 | 0 |
| | 2.0 | 5 | 5 | 0 | 0 |
| | 1.0 | 5 | 4 | 0 | 0 |
| 246 | 3.0 | 5 | 5 | 1 | 0 |
| | 2.0 | 5 | 5 | 0 | 0 |
| | 1.0 | 5 | 4 | 0 | 0 |
| 248 | 3.0 | 5 | 5 | 0 | 0 |
| | 2.0 | 5 | 5 | 0 | 0 |
| | 1.0 | 4 | 4 | 0 | 0 |
| 257 | 3.0 | 5 | 5 | 0 | 0 |
| | 2.0 | 5 | 5 | 0 | 0 |
| | 1.0 | 4 | 4 | 0 | 0 |
| 260 | 3.0 | 5 | 5 | 0 | 0 |
| | 2.0 | 5 | 5 | 0 | 0 |
| | 1.0 | 4 | 4 | 0 | 0 |
| 263 | 3.0 | 5 | 5 | 0 | 0 |
| | 2.0 | 5 | 5 | 0 | 0 |
| | 1.0 | 4 | 4 | 0 | 0 |

What is claimed is:

1. A cyanoketone derivative of the following formula (1)

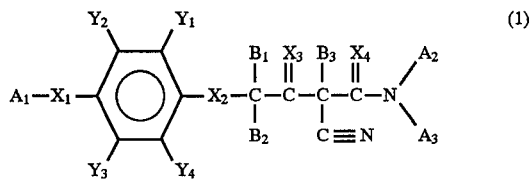

wherein $A_1$ is a substituted or unsubstituted phenyl or naphthyl group, or a substituted or unsubstituted heterocyclic group selected from the group consisting of a 5-membered ring, a 6-membered ring, a 5- and 6-membered fused ring group and a 6- and 6-membered fused ring group, wherein said heterocyclic group contains from 1 to 3 hetero atoms selected from the group consisting of oxygen, nitrogen and sulfur or mixtures thereof, substituents of said substituted phenyl, naphthyl and heterocyclic groups being selected from the group consisting of a halogen atom, an alkyl group having 1 to 4 carbon atoms, a halogenoalkyl group having 1 to 4 carbon atoms, an alkoxy group having 1 to 4 carbon atoms, an alkylthio group having 1 to 4 carbon atoms, an alkoxycarbonyl group having 2 to 6 carbon atoms, a nitro group and a cyano group; each of $X_1$, $X_2$, $X_3$ and $X_4$ is independently an oxygen or sulfur atom; each of $B_1$, $B_2$ and $B_3$ is independently a hydrogen atom or alkyl group having 1 to 6 carbon atoms; each of $Y_1$, $Y_2$, $Y_3$ and $Y_4$ is independently a hydrogen atom, a halogen atom or alkyl group having 1 to 6 carbon atoms; and each of $A_2$ and $A_3$ is independently selected from the group consisting of a hydrogen atom, a substituted or unsubstituted alkyl group having 2 to 6 carbon atoms, an alkenyl group having 2 to 6 carbon atoms, an alkoxy group having 1 to 4 carbon atoms, an alkylthio group having 1 to 4 carbon atoms, an alkoxycarbonyl group having 1 to 6 carbon atoms, a cyano group and a group as defined in $A_1$; substituents of said substituted alkyl group being selected from the group consisting of a halogen atom, an alkoxy group having 1 to 4 carbon atoms, an alkylthio group having 1 to 4 carbon atoms, a cyano group, a phenyl group and a heterocyclic group of a 5- or 6-membered ring; provided that both $A_2$ and $A_3$ can form a saturated or unsaturated ring of from 2 to 8 carbon atoms which may contain at least one additional nitrogen atom or oxygen atom, and that when $B_1$ is a hydrogen atom and $B_2$ is said alkyl group, the compound of the formula (1) is an R- or S-enantiomer with regard to the asymmetric carbon to which $B_1$ and $B_2$ are bonded or a mixture of these enantiomers.

2. A cyanoketone derivative of claim 1 wherein $A_1$ is said substituted or unsubstituted heterocyclic group.

3. A cyanoketone derivative of claim 1 wherein all of $X_1$, $X_2$, $X_3$ and $X_4$ are oxygen atoms.

4. A cyanoketone derivative of claim 1 wherein all of $Y_1$, $Y_2$, $Y_3$ and $Y_4$ are hydrogen atoms.

5. A cyanoketone derivative of claim 1 wherein $B_1$ is an alkyl group.

6. A cyanoketone derivative of claim 1 wherein both of $B_2$ and $B_3$ are hydrogen atoms.

7. A cyanoketone derivative of claim 1 wherein $A_2$ and $A_3$ together form said saturated or unsaturated ring which may contain additional nitrogen or oxygen hetero atom.

8. A herbicidal composition comprising a herbicidally effective amount of a cyanoketone derivative of claim 1 and an inert carrier.

9. A method of inhibiting the growth of gramineous weeds comprising applying a herbicidally effective amount of the cyanoketone derivative of claim 1 to the locus of weed growth.

10. The method of claim 9, wherein said cyanoketone derivative is applied to the soil.

11. The method of claim 9, wherein said cyanoketone derivative is applied to the foliage of said weeds.

12. A cyanoketone derivative of claim 2 wherein said heterocyclic group is selected from the group consisting of furyl, thienyl, pyrrolyl, imidazolyl, pyrazolyl, oxazolyl, thiazolyl, isooxazolyl, isothiazolyl, pyridyl, pyranyl, thiopyranyl, pyrazinyl, pyrimidinyl, triazinyl, benzofuranyl, benzothienyl, indolyl, benzimidazolyl, benzothiazolyl, benzoxazolyl, oxazolopyridinyl, thiazolopyridinyl, quinolyl, quinoxalinyl and quinazolinyl.

13. A cyanoketone derivative of claim 2 wherein said heterocyclic group contains from 1 to 3 nitrogen atoms.

14. A cyanoketone derivative of claim 13 wherein the heterocyclic group is selected from the group consisting of pyrrolyl, imidazolyl, pyrazolyl, pyridyl, pyranyl, pyrazinyl, pyrimidinyl, triazinyl, indolyl, benzimidazolyl, quinolyl, quinoxalinyl and quinazolinyl.

15. A cyanoketone derivative of claim 7 wherein $A_2$ and $A_3$ together with the nitrogen atom to which they are bonded form a ring selected from the group consisting of ethyleneimino, pyrrolidyl, pyrrolyl, pyrrolinyl, pyrazyl, pyrazolinyl, imidazolyl, triazolyl, piperidino, morpholino, piperazinyl, and indolyl.

16. A cyanoketone derivative of claim 2 wherein each of $X_1$, $X_2$, $X_3$ and $X_4$ are oxygen atoms; each of $Y_1$, $Y_2$, $Y_3$ and $Y_4$ are hydrogen atoms; $B_1$ is an alkyl group; $B_2$ and $B_3$ are each hydrogen atoms; and $A_2$ and $A_3$ together with the nitrogen atom to which they are bonded form a saturated or unsaturated ring which may contain additional nitrogen or oxygen hetero atom.

17. A cyanoketone derivative of claim 1 wherein $A_1$ is a substituted or unsubstituted heterocyclic group wherein the heterocyclic group is selected from the group consisting of furyl, thienyl, pyrrolyl, imidazolyl, pyrazolyl, oxazolyl, thiazolyl, isooxazolyl, isothiazolyl, pyridyl, pyranyl, thiopyranyl, pyrazinyl, pyrimidinyl, triazinyl, benzofuranyl, benzothienyl, indolyl, benzimidazolyl, benzothiazolyl, benzoxazolyl, oxazolopyridinyl, thiazolopyridinyl, quinolyl, quinoxalinyl and quinazolinyl; and wherein $A_2$ and $A_3$ together with the nitrogen atom to which they are bonded form a cyclic group selected from the group consisting of ethyleneimino, pyrrolidyl, pyrrolyl, pyrrolinyl, pyrazyl, pyrazolinyl, imidazolyl, triazolyl, piperidino, morpholino, piperazinyl and indolyl.

18. A herbicidal composition of claim 8 in the form of a wettable powder or granules comprising from 1 to 80 parts by weight of the cyanoketone derivative of formula (1), 5 to 98 parts by weight of an inert solid carrier and 1 to 15 parts by weight of a surfactant.

19. A herbicidal composition of claim 8 in the form of an emulsifiable concentrate comprising from 75 to 20 parts by weight of the cyanoketone derivative of formula (1), 10 to 20 parts by weight of a surfactant and 15 to 60 parts by weight of a solvent in which the cyanoketone derivative is soluble.

20. A herbicidal composition of claim 8 in the form of a flowable agent comprising a suspension of from 20 to 50% by weight of the cyanoketone derivative of formula (1) in water and a dispersant in an amount effective to disperse the suspended cyanoketone derivative in water.

21. A method of claim 9 which comprises applying from about 0.05 to 20.0 kilograms per hectare of the cyanoketone derivative to the locus of weed growth.

22. 1-cyano-1-piperidylcarbonyl-3-[4-(2-chloro-4-trifluoromethylphenoxy)phenoxy]-2-butanone.

23. A cyanoketone derivative of formula (1) according to claim 1 which is selected from the group consisting of 1-cyano-1-piperidinocarbonyl-3-[4-(2-chloro-4-trifluoromethylphenoxy)phenoxy]-2-butanone, 1-cyano-1-piperidinocarbonyl-3-[4-(3-chloro-5-trifluoromethyl-2-pyridyloxy)phenoxy]-2-butanone, 1-cyano-1-(N-methyl-N-dichlorophenyl)aminocarbonyl-3-[4-(2-quinoxalyloxy)phenoxy]-2-butanone, and 1-cyano-1-(N,N-dibutyl)aminocarbonyl-3-[4-(3-chloro-5-trifluoromethyl-2-pyridyloxy)phenoxy-2-butanone.

* * * * *